(12) United States Patent
Hyde et al.

(10) Patent No.: US 9,155,591 B2
(45) Date of Patent: Oct. 13, 2015

(54) TREATMENT LIMITER

(75) Inventors: Roderick A. Hyde, Livermore, CA (US); Muriel Y. Ishikawa, Livermore, CA (US); Edward K. Y. Jung, Bellevue, WA (US); Eric C. Leuthardt, St Louis, MO (US); Royce A. Levien, Lexington, MA (US); Robert W. Lord, Seattle, WA (US); Mark A. Malamud, Seattle, WA (US); Nathan P. Myhrvold, Medina, WA (US); Dennis J. Rivet, St. Louis, MO (US); John D. Rinaldo, Jr., Bellevue, WA (US); Michael A. Smith, San Gabriel, CA (US); Clarence T. Tegreene, Bellevue, WA (US); Lowell L. Wood, Jr., Livermore, CA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1736 days.

(21) Appl. No.: 11/522,493

(22) Filed: Sep. 14, 2006

(65) Prior Publication Data

US 2008/0071570 A1    Mar. 20, 2008

(51) Int. Cl.
```
G06Q 50/22    (2012.01)
G06Q 50/24    (2012.01)
A61B 19/08    (2006.01)
A61B 19/12    (2006.01)
A61B 19/00    (2006.01)
```

(52) U.S. Cl.
CPC ............... *A61B 19/08* (2013.01); *G06Q 50/22* (2013.01); *A61B 19/12* (2013.01); *A61B 19/40* (2013.01)

(58) Field of Classification Search
USPC ........................................... 705/2–3
See application file for complete search history.

(56) References Cited

U.S. PATENT DOCUMENTS

| | | | | |
|---|---|---|---|---|
| 4,938,233 | A * | 7/1990 | Orrison, Jr. ................... | 128/849 |
| 5,833,608 | A * | 11/1998 | Acker ........................... | 600/409 |
| 6,567,687 | B2 * | 5/2003 | Front et al. ................... | 600/426 |
| 2002/0065461 | A1 * | 5/2002 | Cosman ....................... | 600/426 |
| 2004/0002641 | A1 * | 1/2004 | Sjogren et al. ................ | 600/407 |
| 2004/0056478 | A1 * | 3/2004 | Bruce ............................ | 283/81 |
| 2006/0142631 | A1 * | 6/2006 | Meretei ........................... | 600/12 |
| 2006/0174895 | A1 * | 8/2006 | Ferguson et al. ............. | 128/845 |
| 2007/0078678 | A1 * | 4/2007 | DiSilvestro et al. ............. | 705/2 |

OTHER PUBLICATIONS

Liu et al. "In-vitro investigation of blood embolization in cancer treatment using magnetorheological fluids." Journal of Magnetism and Magnetic Materials, 225(2001), p. 2009-217.*

(Continued)

*Primary Examiner* — Fonya Long
*Assistant Examiner* — Kristine Rapillo

(57) ABSTRACT

One aspect relates to limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated. Another aspect relates to configuring at least a portion of a treatment limiter mechanism at least partially in response to attempting to treat at least a portion of an individual associated with the treatment limiter mechanism.

22 Claims, 13 Drawing Sheets

(56) References Cited

OTHER PUBLICATIONS

Liu et al. "In-vitro investigation of blood embolization in cancer treatment using magnetorheological fluids." Journal of Magnetism and Magnetic Materials, 225(2001), p. 2009-217.*

Bell, Richard C.; Zimmerman Ph.D., Darin T.; Vavreck Ph.D., Andy; "Properties of Magnetorheological Fluids"; Bell—Research at PSA; printed on Sep. 8, 2006; pp. 1-4; located at http://www.personal.psu.edu/faculty/r/c/rcb155/Research/R_MR_Fluids.htm.

biosyntech.com; "BST-Ossifix™ for Bone Structural Support in Weakened or Fractured Bones"; Hydrogel Technology for Bone Structural Support; bearing a date of 2005; printed on Sep. 8, 2006; pp. 1; located at http://www.biosyntech.com/en/expertise/orthopedics/?BST=Ossifix.

Karoub, Jeff; "Patent Promises to Place Smart Scalpels in Surgeons' Hands"; Small Times; bearing a dates of Jan. 30, 2003 and 2006; printed on May 4, 2006; pp. 1-3; located at http://www.smalltimes.com/document_display.cfm?document_id=5405&keyword=Patent%20and%20Promises%20and%20to%20and%20Place%20and%20Smart%20and%20Scalpels%20and20in%20and%20Surgeons%27%20and%20Hands&summary=1&startsum=1.

Patry, Dr. Johanne; Borsclair, Jocelyn; "The Magic of Magnetorheologic Fluids"; pp. 1; located at http://www.iop.org/Our_Activities/Schools_and_Colleges/Teaching_Resources/Other%20Resources/Online_Resources/Physics%20on%20Stage%203/file_6550.pdf#search=%22The%20Magic%20of%20Magnetorheologic%20Fluids%22.

"Session Z8—Polarization Dynamics in Ferroelectrics IV: Structure and Dynamics in Perovskite Dielectrics."; printed on Sep. 8, 2006; pp. 1-5; located at http://flux.aps.org/meetings/YR01/MAR01/abs/S8880.html.

Simon, D.A.; O'Toole, R.V.; Blackwell, M.; F.; Digioia, A.M.; Kanade, T.; "Accuracy Validation in Image-Guided Orthopedic Surgery"; pp. 1-8; located at www.gaitech.net/Accuracy.pdf.

"Tiny Tools Give New Meaning to 'Cutting Edge'"; Science Daily; bearing dates of Apr. 1, 1999 and 1995-2006; printed on May 4, 2006; pp. 1-3; located at http://www.sciencedaily.com/releases/1999/04/990401061345.htm.

\* cited by examiner

TREATMENT LIMITER

TECHNICAL FIELD

Certain aspects of this disclosure can relate to, but are not limited to, treatment limiter mechanisms and/or associated techniques.

DETAILED DESCRIPTION

Figure 1:
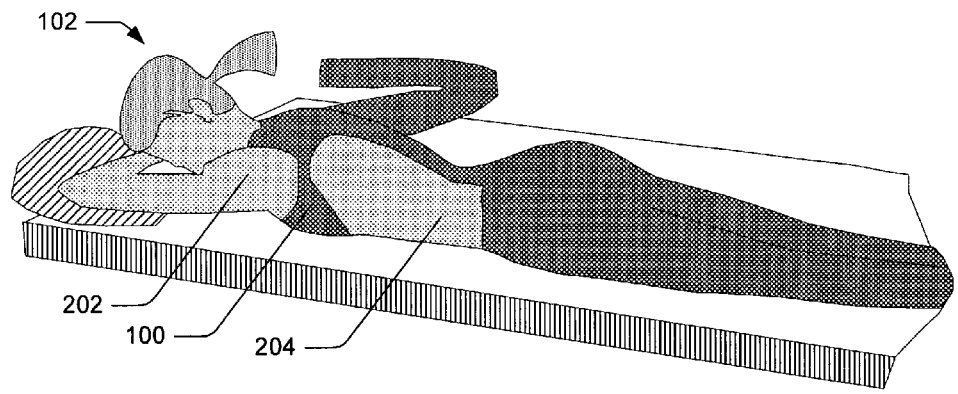
FIG. 1 is a diagram of one embodiment of a treatment limiter mechanism.

At least certain portions of the text of this disclosure (e.g., claims and/or detailed description and/or drawings as set forth herein) can support various different claim groupings and/or various different applications. Although, for sake of convenience and understanding, the detailed description can include section headings that may generally track various different concepts associated with claims or general concepts contained therein, and is not intended to limit the scope of the invention as set forth by each particular claim. It is to be understood that support for the various applications or portions thereof thereby can appear throughout the text and/or drawings at one or more locations, irrespective of the section headings.

1. Certain Embodiments of a Treatment Limiter Mechanism

Certain aspects of this disclosure can relate to a number of embodiments of an at least one treatment limiter mechanism 100, which can be used to ensure that medical, dental, veterinarian, operations, pharmaceutical, emergency, maintenance, and/or other such treatment(s) to be performed on an individual 102 (e.g., a patient or other person receiving treatment) is indeed being performed as desired and/or planned. Additionally, certain embodiments of the treatment limiter mechanism 100 can be configured to ensure the treatment in certain instances is being applied at the appropriate or planned location(s), and in certain instances is not being performed on the wrong, undesired, and/or unplanned location.

Certain embodiments of the treatment limiter mechanism 100 may be intended to be worn by, or positioned relative to, the individual 102. Certain embodiments of the treatment limiter mechanism 100 should be configured as to make it obvious, or relatively straightforward, for a treating person to determine where to treat the individual 102 as compared with, conversely, where not to treat the individual. Ensuring that certain embodiments of the treatment limiter mechanism 100 can allow treating the individual 102 at the appropriate or planned location (e.g., by a treating person or process) can be divided into at least two aspects. Firstly, certain embodiments of the treatment limiter mechanism 100 may be utilized to increase the likelihood that the treating person or process does not treat the individual 102 at an incorrect location. Secondly, certain embodiments of the treatment limiter mechanism 100 may be utilized to increase the likelihood that the treating person or process does treat the correct location.

While it is possible that certain treating person(s) or process(es) could feasibly ignore or override the treatment limiter mechanism 100, and thereby continue to treat the individual at an incorrect or unplanned location (or alternately not treat the individual 102 at the correct or planned location). It is envisioned that certain embodiments of the treatment limiter mechanism 100 can make it considerably easier, or more obvious, for the treating person or process not to treat the incorrect or unplanned location, or alternately to treat the correct or planned location. Within this disclosure, the term "treatment limiter mechanism" can, depending on context, apply to a mechanism that can be configured, depending on context, to either treat the incorrect or unplanned location, or alternately not treat the correct or planned location.

At least a portion of certain embodiments of the treatment limiter mechanism 100, as described in this disclosure, can be configured at least partially in response to attempting to treat at least a portion of an individual associated with the treatment limiter mechanism. For example, certain embodiments of the treatment limiter mechanism 100 can change some characteristics which could make it easier to limit treatment in an undesired or unplanned location such as: color, hardness or softness (such as to make it respectively more difficult or easier to cut or penetrate), display text, images, or other information, etc.

Certain embodiments of the treatment limiter mechanism 100 can thereby indicate where the treatment is to be performed. There may be a variety of techniques by which such an indication that the treatment can be provided at a particular location that can include, but are not limited to: having the material of the treatment being made of a particular color, texture, appearance, absorbance characteristic, etc.; leaving an area to be treated uncovered; allowing at least some of the material or fabric of the treatment limiter mechanism 100 to be able, or configured to be cut away or removed by a tool such as scissors or scalpels; and/or providing an indication to at least one treatment tool that it is situated in a desired location relative to the individual using such illustrative but not-limiting mechanisms that may interrelate with the treatment limiter mechanism as fiducials, etc. as described in this disclosure. By comparison, there may be a variety of techniques by which such an indication that the treatment should not be provided at that location of the individual that can include, but are not limited to: having the material of the treatment being made of a suitable color (e.g., red); leaving an area to be treated covered and difficult to uncover; the material not being able to be cut away or removed by a tool such as scissors or scalpels; providing an indication to at least one treatment tool that the tool is not situated in a desired location relative to the individual (such as by using fiducials or other position-providing mechanisms, etc.), These examples are intended to be illustrative in nature but not limiting in scope, and will be clarified by further examples as described in this disclosure.

Certain embodiments of the treatment limiter mechanism 100, as described in this disclosure, may be configured to be applied to a variety of individuals that can include, but are not limited to: people, animals, organisms, and/or plants, etc. While certain embodiments of the treatment limiter mechanism 100, such as are described in this disclosure, may be described as being applicable to a particular type of individual 102 such as people, it can be assumed, unless otherwise indicated and/or obviously inapplicable, that the treatment limiter mechanism can be modified to be applicable to other types of individuals such as animals, plants, or organisms.

Certain embodiments of the treatment limiter mechanism 100, which can be applied to such individuals as organisms and/or plants, can ensure a suitable diet, treatment, regimen, or other factors can be provided to the individual organism and/or plant such as may either enhance/promote growth or maintenance, or alternately which may harm, kill, or perform some other "treatment" relative to certain organisms or plants. In certain instances, the treating person or process (e.g., researcher, etc.) associated with such individuals as organisms and plants can be alerted in a variety of ways if the treatment is in some manner falling outside of desired or planned criteria.

FIG. 1 shows one embodiment of the treatment limiter mechanism 100, which can be applied to the individual 102 being treated. Such treatment as may utilize certain embodiments of the treatment limiter mechanism 100 can occur in such illustrative but not limiting locations as: hospitals, clinics, emergency care situations, medical office, dental offices, research centers, etc. The illustrated individual 102 in this instance is a woman undergoing treatment on her left arm 202 and/or left torso 204, both of which are illustrated as remaining uncovered by the treatment limiter mechanism 100. In FIG. 1, the individual's right arm is illustrated as being covered by a sleeve portion of the treatment limiter mechanism 100 (including enclosing her hand); as is the remainder of her body with the exception of her left arm and her head. Other embodiments of the treatment limiter mechanism 100 can be provided in which desired or planned portion(s) of the individual's body remains uncovered for treatment, while at least some undesired or unplanned portion(s) of the individual's body remains covered to limit treatment.

As such, considering the treatment limiter mechanism 100 as described with respect to FIG. 1, regardless of the position in which the individual 102 is, or has been positioned into (e.g., standing up, lying on her stomach, lying on her side, lying on her back, etc.), there are only certain exposed portions which can indicate, depending on context, those portions that should be treated. For example, the exposed portion(s) in the instance of FIG. 1, for example, can include one arm 202 and one torso portion 204. The exposed portion(s) thereby indicate to the treating person or process that body part, bone, bone fragment, organ, skin region, etc. that is to be treated. The likelihood that a treating person or process would continue to treat a body part of the individual that is indicated not to be treated, such as being covered by the treatment limiter mechanism 100 (e.g., the right arm and/or right torso as described with respect to FIG. 1) is thereby considerably reduced regardless of experience, skill level, language, etc. of the treating person. It should be evident, to the treating person or process not to treat a body part covered by the treatment limiter mechanism 100 that is indicated as not to treat.

While the embodiment of the treatment limiter mechanism 100 as described with respect to FIG. 1 includes a body suit, it is envisioned that a variety of materials and/or fabrics can be utilized while remaining within the scope of the present disclosure. For example, such illustrative but not-limiting materials as fabrics, tape, surgical tape, paints, colorings, solids, shields, sheets, displays, etc. can, depending on context, be utilized as certain embodiments of the treatment limiter mechanism 100 as described in this disclosure. Certain embodiments of the treatment limiter mechanism 100 can be intended to be worn with other clothes, such as hospital garb or pajamas. Certain embodiments of the treatment limiter mechanism 100 can also utilize a variety of materials or portions such as fabric, body stocking material, coatings, inserts, implants, magnetorheologic fluid, and/or a variety of materials or combination of materials such that when worn by the individual 102, the treatment limiter mechanism 100 is intended to either indicate where not to treat by one or more treatment tools, or alternately where not to treat, such as by limiting access to treatment by the one or more treatment tools.

Those portions of the individual that are not at least partially covered by certain embodiments of the treatment limiter mechanism 100 (e.g., are uncovered) thereby can correspond to those locations of the individual 102 that are to be treated. By comparison, those portions of the individual that are at least partially covered by certain embodiments of the treatment limiter mechanism 100 can correspond to those locations of the individual that are not to be treated by the treating person or process. Certain portions of the individual may be treated at locations in which at least a portion of the treatment limiter mechanism 100 can be pushed away, or alternately cut away. Certain embodiments of the treatment limiter mechanism 100 can represent those skin or body part portions of the individual that should not be treated.

The term "treatment tool", whose application may be limited by certain embodiments of the treatment limiter mechanism 100, can be considered as being relatively broad, and can include such illustrative treatment tools which may not be limited to: scalpels, x-ray, radiology, other applied electromagnetic radiation, surgical tools, cutting tools, sawing tools, probing tools, tools configured for application of chemotherapy, etc.

Certain more severe or less reversible treatments should be associated with more obvious or non-overrideable embodiments of the treatment limiting mechanisms 100 as compared to the less severe and/or more reversible treatments. For example, an embodiment of the treatment limiter mechanism 100 may be suitably configured as to be associated with such treatment as surgery of one limb, an important organ, a bone, or a body part, for example, should be configured to make it extremely obvious and/or difficult for the treating person or process (e.g., surgeon) to treat the wrong area or perform the wrong treatment, such as operating on the wrong organ, bone, or body part.

Certain embodiments of the treatment limiter mechanism 100 can be configured for comfort and/or style. Consider that there are a large number of individuals receiving treatment in hospitals, doctor's offices, nursing homes, clinics, homecare, etc. either for a brief duration and/or an extended duration. For instance, certain embodiments of the treatment limiter mechanism can be at least partially selected based at least in part on the individual's treatment, desire, and/or taste. It could be argued (and many patients currently being treated unquestionably believe) that traditional hospital pajamas, for example, are uncomfortable, unstylish, and/or are potentially overly revealing such as to even under certain instances make many of the individuals' 102 stay in the hospital or clinic more uncomfortable and/or more unpleasant. During a variety of treatments, such as an operation and/or when the individual is unconscious, such traditional hospital pajamas may not properly conceal desired or private portions of the individual. Certain embodiments of the treatment limiter mechanism 100 can also be worn in combination with and/or in addition to the traditional hospital pajamas, or other clothing.

Certain portions of certain embodiments of the treatment limiter mechanism 100 may be fabricated from a material that can enhance comfort, warmth, remaining dry, and/or some other aspect. For example, certain patients rooms, doctor's offices, operating rooms, and/or examination rooms may be relatively cold, hot, humid, or otherwise uncomfortable; and certain embodiments of the treatment limiter mechanism 100 can be configured to provide respective warmth or ventilation (e.g., either based on the material selected or alternately by integrating a heating element, not shown). Consider that certain individuals may have an illness, injury, or other condition (e.g., being in shock) which may make them more sensitive to uncomfortable room situations. As such, certain embodiments of the treatment limiter mechanism 100 can thereby be configured, designed, customized, and/or selected for the individual's comfort.

Certain embodiments of the treatment limiter mechanism 100 can also be configured to limit exposure of excessive body parts or skin of the individual 102, if so desired. Such limiting of the exposure may be especially desireable for individuals who are unconscious or anesthetized for a particular duration and/or in some facility for a longer duration such as hospitals, nursing homes, etc. Certain embodiments of the treatment limiter mechanism 100 can provide privacy such as by assuring the individual 102 being treated that certain portions of their skin, their private parts, etc. may not be exposed to the treating person(s) or others during certain treatments not relating to those exposed portions. Certain embodiments of the treatment limiter mechanism 100 can be worn in addition to or in combination with the standard treatment, hospital, and/or surgical clothing. As such, certain individuals that are wearing certain embodiments of the treatment limiter mechanism 100 may feel more comfortable, stylish, and/or more at home than with certain traditional hospital clothing.

Certain embodiments of the treatment limiter mechanism 100 can also colored, be patterned, shaped, designed, etc. to provide at least some minimal fashion, which would likely be preferred to be worn by the individual as compared to the traditional hospital garb. Considering that certain individuals are being treated in hospitals, nursing homes, at home, etc. for extended durations, it might be highly desirable to improve the appearance, feelings, style, comfort, etc. of certain embodiments of the treatment limiter mechanism 100 during the treatment of the individual, however extended. Considerable usage of certain "stylish" embodiments of the treatment limiter mechanism 100 in such facilities as hospitals, nursing homes, etc. can also act to make such facilities more attractive and pleasant, in general.

Certain embodiments of the treatment limiter mechanism 100 may be utilized with surgical tape and/or other tape. Surgical tape can be applied to an individual such as a surgical patient in an area in which they are to be operated. Incisions can be applied through the surgical tape along with the skin, and perhaps lower muscle, fat, and other layers. Certain embodiments of the surgical tape can contain information or images relating to the surgery.

Certain embodiments of the treatment limiter mechanism 100 can contain a variety of image information, such as a position of an organ, body part, bone, etc. For example, certain embodiments of the treatment limiter mechanism, such as a tape, body stocking, fabric, etc. can be patterned with the outline or image of an organ such as heart, kidney, etc.; or alternately a bone, bone fragment, or body part which may be undergoing treatment.

Certain embodiments of the treatment limiter mechanism 100 can thereby be configured to provide a variety of functional information, text, images, etc. about the individual, the internals of the individual, the treating person(s), and/or the treatment of the individual 102. For example, certain embodiments of the treatment limiter mechanism 100 can provide a description of the treatment to the individual, information about the individual and/or the treating person, locations of organs, bones, or other body parts, etc. associated with the treatment, etc. similar to as described in this disclosure with respect to FIGS. 10 and/or 11. For instance, certain embodiments of the treatment limiter mechanism 100 can be provided with an image or representation of bones, body parts, etc. of the individual 102 such as may be useful for the treating person(s) or process(es) during treatment of the individual, during an explanation of the treatment by the treatment person to the individual; or alternatively may be useful for the individual 102, friends, family, etc. in understanding the treatment.

Consider that a number of people, such as patients in hospitals, clinics, doctor's offices, nursing homes, etc., are to some degree unsure or uncertain as to the scope, location, and/or other aspects of their treatment. Such uncertainty may often result from the treating person's inability to describe the treatment. Such uncertainty certainly limits the value of the individual's concurring with or agreeing with the treatment. By using certain embodiments of the treatment limiter mechanism 100 that are configured to display a condition, location, body part, bone, bone fragment, organ, etc., the individual may better understand the treatment as well as consent to the treatment. By using certain embodiments of the treatment limiter 100 that can include treatment information such as images of internal organs, bones, bone fragments, body parts, etc. that are to be treated, as well as their condition, the individual being treated will likely have a greater understanding of their treatment, and might be able to converse more intelligently with the treating person(s) or process(es) as well as have more confidence in the treating person, process, treatments, and/or diagnosis.

The range of images that can be provided can vary considerably from still images that represent a general condition of a portion of the individual to a moving image which displays a number of organs, bones, or other body parts. A variety of imaging, photographic, scopic, x-ray, MRI, and/or other technologies may be utilized for the imaging, many of which are known to be capable of imaging and/or have commercially available imaging versions. Certain embodiments of the treatment limiter mechanism 100 may utilize one more treatment limiter controller 97 as described with respect to FIG. 2 for one or more activities including, but not limited to: sensing, imaging, data processing, communicating, networking, etc. Certain embodiments of the treatment limiter controller 97 can be integrated in or otherwise included in the treatment limiter mechanism, and can utilize such sensing-related devices as motes, which are generally understood and are made commercially available by such companies as Crossbow Technology, Inc., and Intel.

There may be a number of reasons why the treating person(s) or process(es) could treat the individual 102 at an incorrect location of the individual; and the reasons described in this disclosure are intended to be illustrative in nature and not limiting in scope. Certain embodiments of the treatment limiter mechanism 100 may allow interaction between the individual 102 and the treating person or process to ensure, prior to treatment, that the treatment will be as desired, and to the desired locations relative to the individual. As such, the individual 102 could be assured by the treating person that the treatment (and location thereof) as described by the treating person or process, and confirmed by the configuration of the treatment limiter mechanism 100 is proper, prior to the treatment. By the treating person discussing or explaining the treatment to the individual, it is likely that the individual can act as a double-check on the treatment to ensure the correct treatment is being performed at the correct location of the individual.

Certain embodiments of the treatment limiter mechanism 100 may thereby be configurable to limit the potential of the treating person or process making a mistake as to the actual location of the treatment. Consider that often the individual 102 being treated in a hospital, clinic, doctor's office, nursing home, etc. may be passed between a number of the treating person(s), doctors, dentists, researchers, orderlies, technicians, nurses, operations, process(es), etc. during their treatment. For example, in a hospital, the patient-individual may during an operation be transferred from their room via one or more waiting rooms to an operating room, in which the individual may be assigned to the care of a number of treating person(s), process(es) etc. When, in the operating room, at least some other treating person(s) or process(es) may come in contact with or be applied to the individual 102. There may thereby be some confusion as to treatment during such hand-offs between treating person(s) or process(es).

Certain embodiments of the treatment limiter 100 can thereby be configured to improve the probability that the individual will receive treatment, as agreed upon or discussed, even though they are passed through multiple treating persons, multiple treatments, and/or at different times. Consider that one or more treatments, analysis, and/or operations may often be performed in succession; such as treating a surgery patient's (i.e., the individual's) head, then the surgery patient's right leg, then the surgery patient's left hand, etc. It may be desired to reduce the possibility that the treating person would forget the location of the subsequent treatment, such that later surgeries might be performed on the improper arm, leg, organ, etc.

In certain instances, it may be difficult to ascertain with sufficient certainty where an internal organ or body part, bone, or organ is situated within the body. For instance, the body part may tend to shift or become repositioned such as during an organ shift, a bone fracture, or a bone break. It may be difficult to ensure that the imaged condition reflects the current condition of the individual under certain circumstances. In certain instances, the treating person such as a surgeon may be fatigued, inexperienced, confused, or even uncertain as to the treatment and/or the location of the treatment. In certain instances, due to movement by and/or repositioning of the individual 102 being treated (e.g., on the operating table), the treating person may be confused as to the particular location for the treatment of the individual 102 (for example, is the treatment to be performed on a particular portion of the individual's 102 right or left). In certain instances, there might be in incorrect interpretation or misread instruction as to the location of the treatment. In certain instances, there might be an inability for the individual 102 being treated to communicate their injury or illness, or a correct location thereof, to the treating person. Such examples could include children, cognitively impaired patients, and animals.

There may be a variety of embodiments of the treatment limiter mechanism 100 as are described within this disclosure, and these treatment limiter mechanisms are intended to be illustrative in nature, but not limiting in scope. The scope of the treatment limiter mechanism 100, as described in this disclosure, depends on context and thereby is intended to be as described in the appended claims, as interpreted according to the present specification. As such, a variety of embodiments of the treatment limiter mechanism 100 can be configured or used to ensure that the treating person(s) or process(es) perform their treatments such as operations, procedures, and/or practices at the appropriate or planned location of the individual 102; and thereby the probability of performing such potential mis-treatments or undesired treatments is considerably reduced.

It may appear obvious that treating person(s) or process(es) should not treat or be applied to the wrong or unplanned location of the individual 102. It may also appear obvious that the treating person(s) or process(es) should not, if at all possible, make the individual worse off by their treatment then they were prior to the treatment. Unfortunately such scenarios where the treatment may occur at an incorrect location or region do occur such as when the treating person(s) or process(es) treats or is applied to the individual 102 at an incorrect or undesired location. The results of treatment at the wrong location can be devastating to the individual 102. In certain instances, the mis-treatment and/or treatment at the incorrect location can also have devastating results for the reputation of the treating person(s), the process(es), and/or their respective facility. Whether such mistreatment may be a result of inexperience, fatigue, misunderstanding, mistake, a combination of such factors relating to the treating person(s) or process(es), and/or other aspect is often of little importance to the individual 102 or others involved with the treatment. The present disclosure provides a number of embodiments of the treatment limiter mechanism that can further limit the occurrence of such treatments at the wrong location.

Certain embodiments of the treatment limiter mechanism 100 may be associated with a variety and a number of treatments. For example, certain embodiments of the treatment limiter mechanism 100 can be applied to a variety of surgeries, processes, procedures, and/or treatments; and/or slightly modified versions could be applied to a variety of humans, animals, plants, and/or organisms as applied by a variety of treating person(s) or process(es). Certain embodiments of the treatment limiter mechanisms 100 that are intended to be applied to certain plants, organisms, etc. can involve application of a variety of nutrients, chemicals, minerals, insecticides, etc. to the individual 102.

One challenge with certain treatments such as certain surgeries, procedures, etc. is to ensure that the treating person(s) or process(es) is actually performing the desired operation, procedure, treatment, and/or other process at the desired location, and is not treating an inappropriate location. As such, certain embodiments of the treatment limiter mechanism 100 may be configured to limit treatment by the treating person(s) or process(es) to some undesired and/or unplanned region and/or location.

A variety of configurations of the different embodiments of the treatment limiter mechanism 100 may limit the region and/or location of the treatment, in a variety of manners such as described in this disclosure. For example, certain embodiments of the treatment limiter mechanism 100, as described with respect to FIG. 1, can be configured to be a mechanism (e.g., clothing, tape, paint) that can indicate where the treating person(s) or process(es) should treat the individual 102 using colors, marks, or other indications. Certain embodiments of the treatment limiter mechanism 100 can be configured as a bodysuit, a body stocking, or similar device that can be colored are configured to limit treatment of the individual 102 to only particular locations. With certain embodiments of the treatment limiter mechanism 100, the color of at least portions thereof can be changed or configured to reflect the various locations of the treatment.

There may be a variety of materials that can be applied to certain embodiments of the treatment limiter mechanism 100. Certain embodiments of the treatment limiter mechanism 100, as described with respect to FIGS. 1, 3, and 4, for example, can be configured to be primarily mechanical-based. Certain of the mechanical-based embodiments of the treatment limiter mechanism 100, as described with respect to FIGS. 1, 3, and 4, can thereby be configured to limit treatment to prescribed regions of the individual 102 where treatment, surgery, or another medical activity may be performed appropriate considering the particular treatment. For example, it may be desired to limit operations, procedures, or other activities on an unplanned location of the individual 102.

There are intended to be a variety of treating person(s) or process(es) that could each apply certain varied treatment to the individual 102, depending at least in part on such factors as the type of the individual 102, the condition of the individual, and the treatment to the individual. Within this disclosure, the term "treating person" can, depending on context, include but is not limited to: doctors, dentists, veterinarians, emergency responders, surgeons, pharmacists, dentists, emergency care providers, ambulance attendants, clinical or hospital assistants, ski patrols, lifeguards, etc. Certain embodiments of the treatment limiter mechanism 100, as described in this disclosure, can be configured as clothes; and thereby can be configured and/or made from a material to provide warmth, coolness, moisture or sweat wicking, etc.

Figure 3:
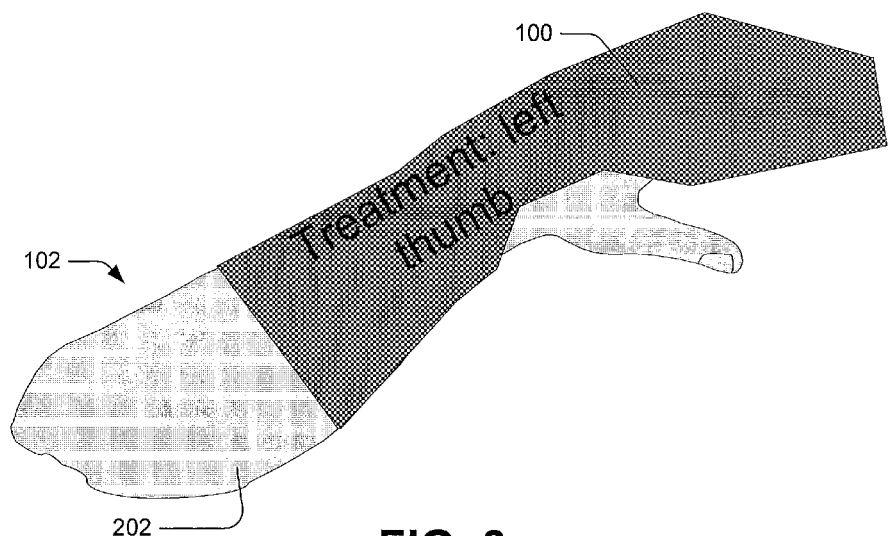
FIG. 3 is a diagram of another embodiment of the treatment limiter mechanism.
Figure 4:
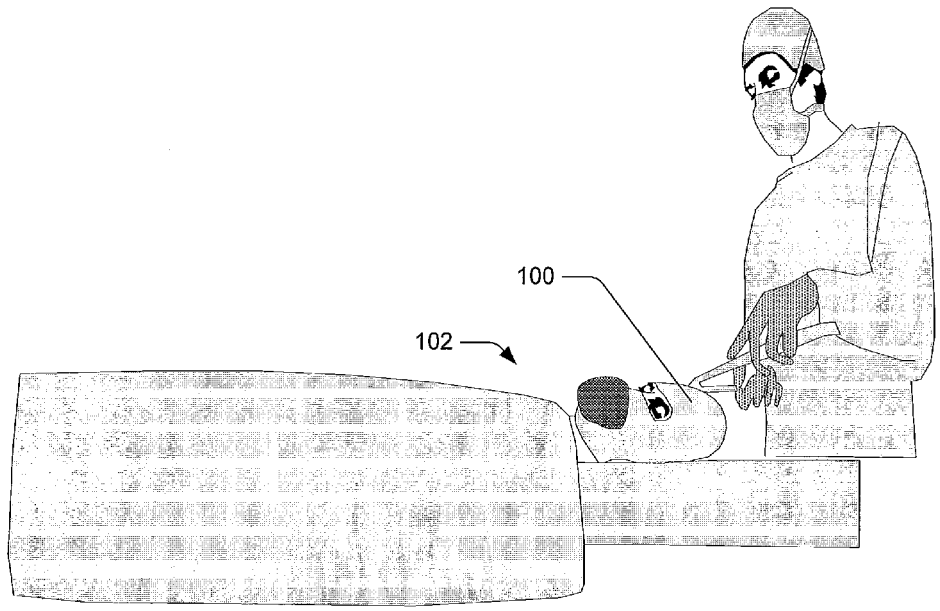
FIG. 4 is a diagram of yet another embodiment of the treatment limiter mechanism.

While FIG. 1 illustrates one embodiment of the treatment limiter mechanism 100 that is configured to cover a considerable portion of the body, another embodiment of the treatment limiter mechanism 100 as described with respect to FIG. 3 can be configured to be applied to a relatively small portion of the body, such as an arm. FIGS. 3 and 4 thereby show embodiments of the treatment limiter mechanism 100 that is also mechanically configured to make it difficult and/or obvious to treat the desired or planned location such as the right arm, the head, some other location or region of the body of the individual, and/or at least not treat an undesired or unplanned location. The embodiment of the treatment limiter mechanism as described with respect to FIGS. 3 and 4, however, is intended to be applied to a portion of a body instead of the entire body. For instance, the treatment portion of the individual 102 being treated as described with respect to FIG. 3 may include the left thumb as well as proximal portions, which is to be left exposed to allow for a suitable treatment. Certain embodiments of the treatment limiter mechanism 100 can have text, images, information, etc. provided thereupon as to indicate the location, type of treatment, particulars of the injury or illness, instructions to or from the treating person(s) or process(es), and/or other information that can be provided.

FIG. 4 shows one embodiment of the treatment limiter mechanism 100 that can be applied to the head of an individual, for example. The embodiment of the treatment limiter mechanism 100 can be utilized during typical operations and may include markings, images, etc. as may be useful during treatment such as head surgery. Certain embodiments of the treatment limiter mechanism 100 as described in FIG. 4 can be cut away as desired, while other embodiments could resist cutting or penetration by surgical tools or the like. Certain portions of the treatment limiter mechanism 100 as described with respect to FIG. 4 can be configured with opening for eyes, nose, and/or mouth as may be suitable for the particular treatment.

Certain embodiments of the treatment limiter mechanism 100 as described with respect to FIGS. 1, 3 and/or 4, can involve such materials as nylon, body stocking or bodysuit material, paint, plastic, display material, combinations thereof, modifications thereof, etc. It may be desired that the treatment limiter mechanism can be made, fabricated, or modified with a resilient or tough material that can be difficult, if not impossible, to cut through using conventional medical instruments such as to truly limit treatment in those areas. Certain of the portions of the certain embodiments of the treatment limiter mechanism 100 can be configured to be difficult to cut with typical surgical tools, simple to cut with typical surgical tools, or can change its cuttability with typical surgical tools.

Certain embodiments of the treatment limiter mechanism 100 may also be configured to make it more difficult for certain people to contact certain individuals in an unwanted or undesired manner. For example, traditional hospital garb are notoriously easy to push aside and/or remove from an unconscious, anesthetized, or debilitated individual. Certain embodiments of the treatment limiter mechanism 100 can be configured to at least be more difficult to remove and/or get around or through.

Certain implants, coatings, etc. could be applied to at least portions of certain embodiments of the treatment limiter mechanism 100; such that when applied, the material characteristics of the portion of the treatment limiter mechanism 100 can be altered such as becoming more rigid than the substrate material. Such materials may be configured to be applied to areas to which the treating person should not treat, and thereby make it difficult to treat the individual 102 at that location considering the treating tool(s) that would likely be used for the treatment. Certain embodiments of the treatment limiter mechanism, as described with respect to FIGS. 1, 3, and 4, can be made to include such materials as metal, metal fiber, carbon fiber, fiberglass, plastic, etc. which might be constructed as to be impregnable against such treatment tools as scalpels, cutters, etc. Certain embodiments of the treatment limiter mechanism 100 can thereby be configured, for example, as a body stocking that only covers a portion of the body (e.g., half of body, one or more extremities of the body, a torso of the body, etc.) that may be configured to limit treatment to those areas that are not covered.

Certain embodiments of the treatment limiter mechanism 100 can be configured with such features as holes or pores to be more comfortable or somewhat breathable, as desired. Certain embodiments of the treatment limiter mechanism 100 can be configured, contoured, and/or customized to be suitable for certain types of operations and/or sizes of individuals. As such, many of the considerations of clothing relative to comfort, warmth, coolness, wearability, etc. may also be considered when providing certain embodiments of the treatment limiter mechanism 100. Certain embodiments of the treatment limiter mechanism 100 can be cut away, such as to provide access to and/or indicate a location or region of the individual to be treated.

While certain embodiments of the treatment limiter mechanism 100 can primarily involve only an item of clothing that can limit the location of treatment, other embodiments of the treatment limiter mechanism may additionally involve a computer-based, controller-based, or other mechanism that can work alone or in combination with the clothing, etc. which can control the operation of the treatment limiter mechanism. For instance, certain embodiments of the treatment limiter mechanism 100 can at least partially include the treatment limiter controller 97, as described with respect to FIG. 2, that can used in a manner to electronically-based, controller-based, and/or computer-based limit treatment to the individual 102. A variety of treatment limiter mechanisms that can involve the treatment limiter controller 97 such as are described elsewhere in this disclosure.

Figure 5:
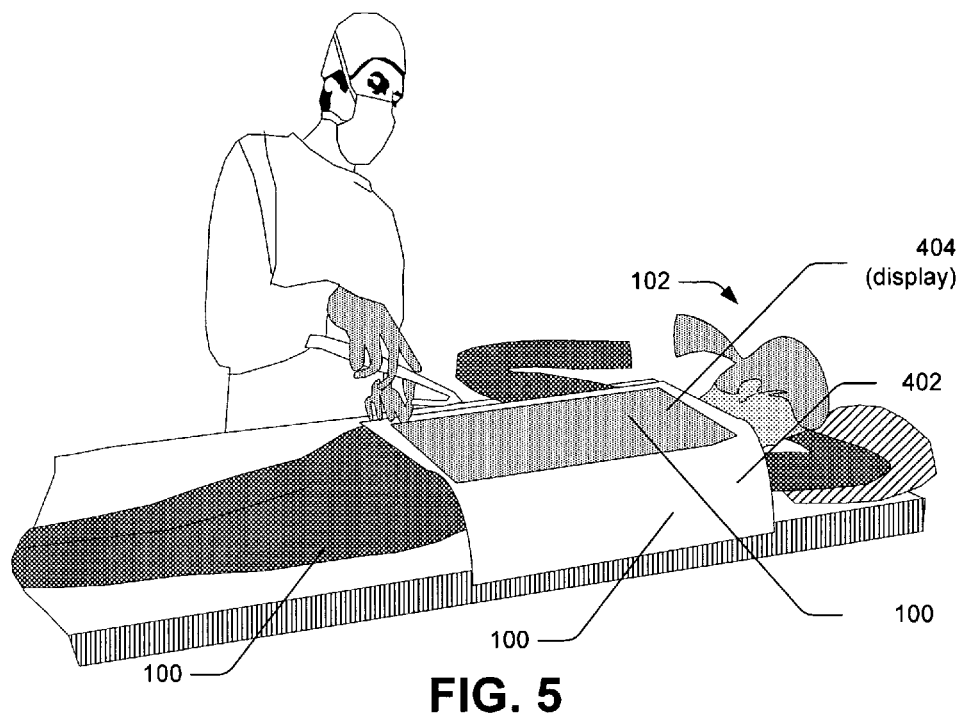
FIG. 5 is a diagram of still another embodiment of the treatment limiter mechanism.

Certain embodiments of treatment limiter mechanism 100 do not need to be worn and/or positioned substantially in contact with the individual. For example, certain embodiments of the treatment limiter mechanism 100 can include a structure build about an operating table. FIG. 5 shows an embodiment of the treatment limiter mechanism 100 that can involve a plate or shield 402 (which may be rigid, flexible, cuttable, non-cuttable, etc.) that may be associated with, for example, a hospital bed or operating table. Certain embodiments of the plate or shield 402 can shield undesired locations of the individual from treatment. Certain embodiments of the shield 402 can include a display 404 which may describe certain aspects, provides certain information, display certain images, etc., about the treatment. A variety of embodiments of the display 404 can be provided extending in complexity to an x-ray, MRI or other still imaging or photographic system to moving-images that can provide a substantially real-time moving image (e.g., using LED, LCD, optical, or other suitable technology or systems) of the treatment regimen. Certain embodiments of the shield 402 embodiment of the treatment limiter mechanism 100 can include components, radiation or electromagnetic radiative devices, displays, elements, etc. which may be associated with the treatment. For instance, certain embodiments of the display 404 can display an outline, a condition, and image, text relating to, and/or other information about a body part, organ, bone, bone fragment, etc. of the individual. Consider a surgery where the position of an organ being operated on is uncertain. For example, the small intestine which is unsecured and relatively mobile within the abdomen, and could have the tendency to move or shift from position to position. As such, to find a particular location relative to the small intestine (e.g., locating a lesion in the small intestine), it may be helpful to have something that will help localize the site when the patient is put in the surgical position. Certain other organs, bones, bone fragments, body parts, etc. also may have the tendency to shift within the individual, to some degree or other. It would be especially desirable to illustrate the location or condition of the organ or bone when such organs or bones shift from a typical location, or a portion of the organ or bone is being treated. In certain instances, detecting an accurate location of the organ or bone can allow less invasive surgeries to be performed, such as where scopes can be utilized to treat a small portion of an organ instead of having to "open the patient up," exposing the entire organ. In addition, by the treating individual being more certain as to the location of organs, bones, etc., treatment can be applied to those locations more directly, and incisions can be cut more accurately to the organ, bone, etc.

Certain embodiments of the display 404 can be applied using a variety of LED, LCD, mote, laser, CRT, or other display technology. Certain embodiments of the images that can be projected and/or emanated from the display 404 can be static, can be moving, and/or can be refreshed at various rates. The type of display, the quality of image, the refresh rate, etc. can be selected based on such factors as the condition, injury, illness, etc. of the individual being imaged; the expense and/or complexity of the technology as associated with the individual, the practice, knowledge, and skill of the treating person, etc.

As such, certain embodiments of the treatment limiter mechanism 100 can perform a variety of functions, some of which may be associated with providing the treatment, while others of which may be associated with limiting the treatment (e.g., do not operate on the covered area, operate on the covered area). Certain embodiments of the operating table, hospital bed, stretcher, etc. can be configured similar to that as described in the pending U.S. patent application entitled: Medical Displaceable Contouring Mechanism, Hyde et al., application Ser. No. 11/503,489, Applicant Serial Number 0306-002-014-000000, filed Aug. 10, 2006 (incorporated herein by reference). Other more conventional embodiments of hospital beds, operating tables, stretchers, supports, etc. could also utilize certain embodiments of the shield 402 as described in this disclosure with respect to FIG. 5.

Certain embodiments of the treatment limiter mechanism 100 (not illustrated) can be applied to the individual by a dentist or dental treating person(s) or process(es) which can change states in a manner to limit access to teeth, fillings, etc., to desired and/or planned locations, as to limit contact with undesired and/or unplanned locations. As such, a variety of embodiments of the treatment limiter mechanism can be configured to be applied to a variety of treatments and/or used by a variety of treatment person(s). Those embodiments of the treatment limiter mechanism 100 that are configured for particular applications should be designed considering those particular applications. For example, those embodiments of the treatment limiter mechanism 100 that are intended to be applied to dental treatments should be configured to at least partially fit within the individual's mouth and cover those areas (teeth etc.) that are not to be treated while keeping those areas (teeth, etc.) that are to be treated uncovered. Certain embodiments of the treatment limiter mechanism 100 can also be configured to perform another activity associated with the treatment, such as dental embodiment of the treatment limiter mechanism 100 may be configured to supply water, and/or collection away spit, dental debris, provide dental cleaning material, hold the tongue in a desired position, provide a display that may be observed remotely, perhaps even by the individual patient and/or the dentist, etc. Certain embodiments of the treatment limiter mechanism 100 associated with dental surgery can even include remote-controlled and/or robotic devices. Consider that certain embodiments of the treatment limiter mechanism could perform such operative processes as drilling, cleaning, brushing, etc. using less obtrusive techniques, and without requiring that the individual reposition themselves and/or open their mouths to provide access to the dentist and/or dental assistant. Certain embodiments of the treatment limiter mechanism could apply a suitable electromagnetic radiation against the teeth, such as could be sensed to determine the internal condition (e.g., cavities, security of crowns, etc.) of the teeth, fillings, inserts, implants, etc.

Figure 6:
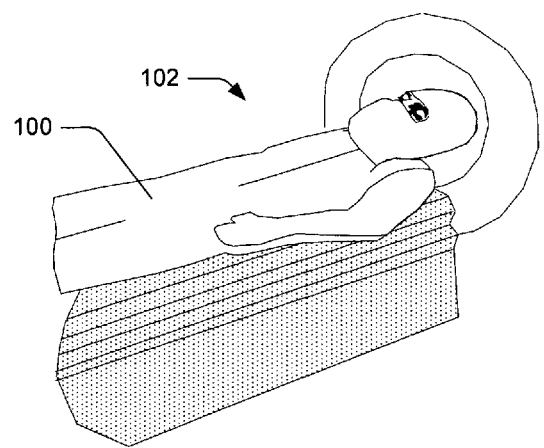
FIG. 6 is a diagram of still another embodiment of the treatment limiter mechanism.

FIG. 6 shows another embodiment of the treatment limiter mechanism 100 that can be applied to be used or worn by the individual 102 receiving such electromagnetic radiation treatment (e.g., MRI treatments, CAT scans, x-ray treatments, optical treatments, infrared treatments, etc.). Certain embodiments of the treatment limiter mechanism 100 can be configured to contour to the individual 102, and may contain some material (e.g., lead or other depending on the treating electromagnetic radiation) which would limit application of the radiation to undesired location(s) of the individual 102. Certain portions of the treatment limiter mechanism 100 may allow the treatment tool (including electromagnetic radiation emitted there from) to be applied to certain portions of the individual to be treated; while shielding other portions of the individual from the treatment tool. Most particularly, only certain portions of the treatment limiter mechanism 100 in which it is desired to allow the desired electromagnetic radiation to pass may be configured without the shielding; while other portions that may be configured to block the electromagnetic radiation.

Certain embodiments of the treatment limiter mechanism 100 can include inserts in which a suitable material that can be configured to shield the individual 102 from the particular electromagnetic radiation as associated with the treatment can be inserted into, or added to, the clothing or material of the treatment limiter mechanism 100. Similar embodiments of the treatment limiter mechanism 100 can thereby be configured to limit application of harmful or undesirable electromagnetic radiation, chemotherapy, chemicals, drugs, etc. to desired, appropriate, and/or planned locations. As such, certain embodiments of the treatment limiter mechanism 100 should be configured-based at least in part on the particulars of the particular treatment.

Figure 7:
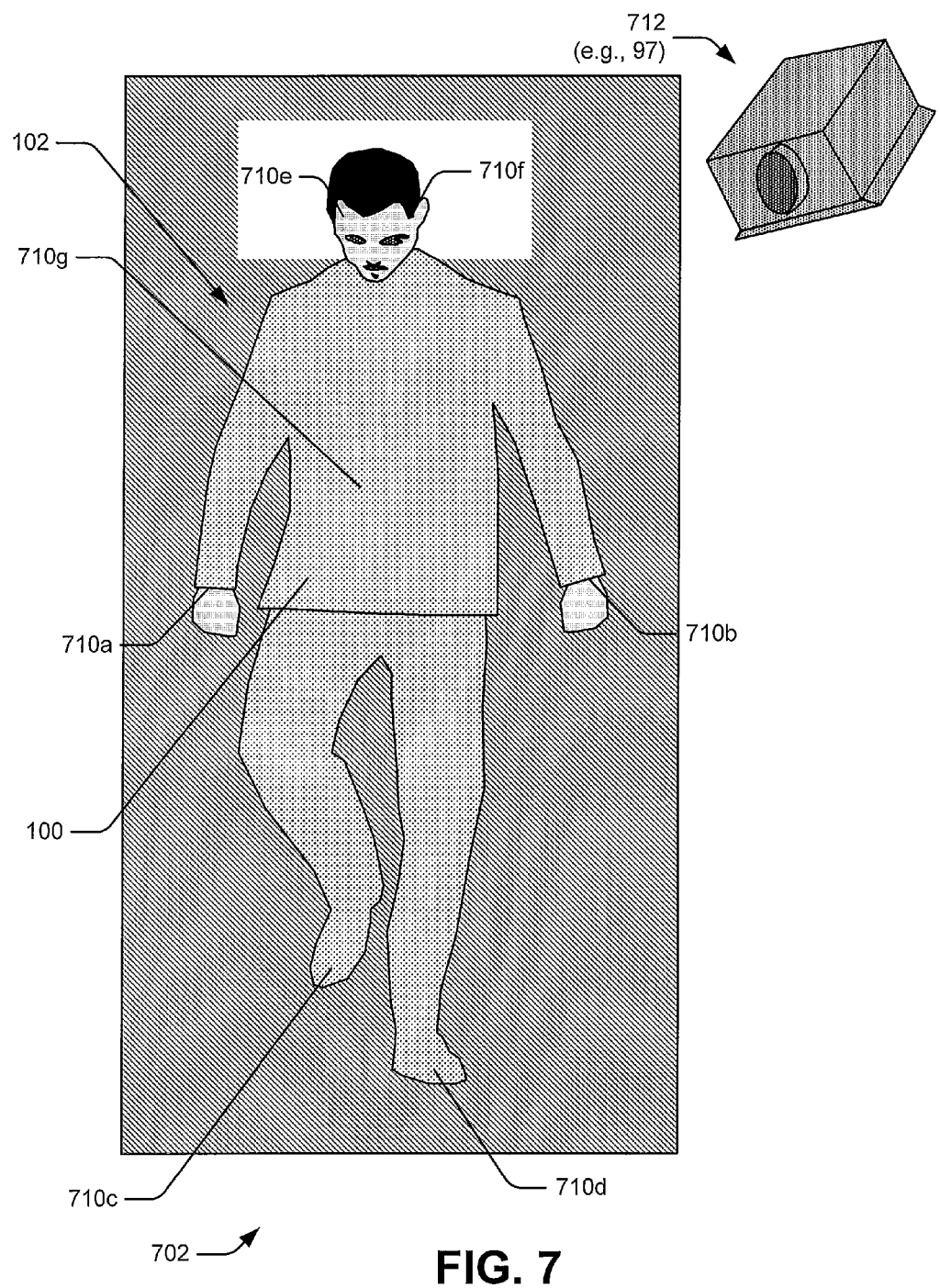
FIG. 7 is a diagram of still another embodiment of the treatment limiter mechanism.

FIG. 7 shows another embodiment of the treatment limiter mechanism 100 that can be configured to utilize one or more relative positioning determiners 702 that can include, but is not limited to, at least one fiducial position associators 710 and at least one treatment/fiducial indicator 712. The at least one fiducial position associator 710 (illustrated in FIG. 7 as 710a to 710g, inclusively) can be configured to allow the treatment limiter mechanism to determine a position of treatment tools, to thereby reduce medical treatment error (perhaps associated with the treatment limiter controller 97). Within this disclosure, fiducials may mean, depending on context, a reference point corresponding to a location on, within, or relative to the individual. Certain embodiments of the fiducial position associators 710 can be positioned relative to the individual. Certain embodiments of the treatment limiter mechanism can utilize at least one fiducial indictor 710 which may include a wireless computing system (such as the treatment limiter controller 97) as described with respect to FIG. 2. As such, certain embodiments of the fiducial position associator(s) 710 can contain data or other information that is associated with at least a part of an individual. For example, one fiducial position associator can be associated with a portion of the body such as the knee, and thereby be configured to provide positional information about the knee perhaps relative to the treatment tool. The at least one fiducial position associator 710 can be positioned at a variety of desired locations relative to the body of the individual 102, depending at least in part on the treatment and the locations thereof. Certain embodiments of the at least one fiducial position associator 710 can be positionally associated with certain body parts, locations, etc. of the individual. For example, as described with respect to FIG. 7, one or more of the fiducial position associators 710 can be positioned relative to the individual 102 at prescribed regions on the individual's body depending on the treatment such as at or proximate the right arm 710a (taken by the individual's point of view in the figure), at or proximate the left arm 710b, at or proximate the right leg 710c, at or proximate the left leg 710d, at or proximate the right head (e.g., above the ear) 710e, at or proximate the left head (e.g., above the ear) 710f, at or proximate the stomach or center of the body 710g, and/or other desired location(s).

Certain embodiments of the treatment limiter mechanism 100 can include a treatment/fiducial indicator 712, which may be associated with a treatment tool, etc., and which can indicate whether it is situated at or nearby a portion of the individual that can be treated, or alternately a portion of the individual that cannot be treated. There can be a variety of mechanisms that can allow the treatment/fiducial indicator 712 to interface with the at least one fiducial position associators 710 in a manner such as to provide positional information about the at least portions of the individual such as relative to the treatment tool. Data, images, and/or information relating to the desired treatment site can be entered with certain embodiments of the fiducial position associator identifying where it is situated relative to the individual (e.g., at the right leg, on the left side of the head, etc.).

Certain embodiments of the fiducial indictor 712 can be associated with the treatment limiter controller 97. Treatment tool information that indicates the position of the treatment tool as derived by the treatment/fiducial indicator 712 can be compared to treatment locating information that indicates where the individual is to be treated. The treatment locating information can be input based at least in part on situating the at least one fiducial position associators 710. The treatment tool information can thereby be compared with the treatment locating information such that the treatment limiter controller 97 has a discernable concept of whether the treatment tool is situated at a location that it can (or has been planned to) treat. If the treatment tool is correctly positioned as indicted by certain embodiments of the treatment limiter mechanism 100, the treatment tool can thereupon be operated and/or positioned as desired at the desired or planned location, as described by certain embodiments of the treatment limiter mechanism 100.

A variety of the relative positioning determiner 702 can be associated with the various embodiments of the fiducial position associators 710 and/or the various embodiments of the treatment/fiducial indicator 712, such as can be used to indicate the position of the treating tool, or the treating person or process, relative to the individual. Such relative positional information can be derived using a variety of relative positioning determiner and the associated technologies including, but not limited to, GPS, imaging, positioning mechanism, etc. The sites of certain embodiments of the fiducial position associators 710 can thereupon be positionally registered by a treating person or process and/or their assistants as to the treatment/fiducial indicator 712 of certain embodiments of the treatment limiter controller 97 of FIG. 2 (such as by using the external imager), as described with respect to FIG. 7. As the individual is repositioned or moved, so will the fiducial position associators 710 associated with at least certain of those body parts of the individual to which the particular fiducial position associator is situated.

Certain embodiments of the fiducial position associators 710, the treatment/fiducial indicator 712, and/or the relative positioning determiner which can be integrated in the treatment limiter controller 97, and can be used in combination with other embodiments or the treatment limiter mechanism 100 as described in this disclosure. Thereupon, the treating person or process can use the treatment tool, which can emit signals, when it is in close proximity to the desired or planned treating location of the individual. If an incorrect site is approached using the certain embodiments of the treatment tool such as provided with the relative positioning determiner, the treatment/fiducial indicator 712 could include an alarm or other indicator which could be actuated in certain instances, thereby alerting the treating person or process. In other embodiments of the treatment limiter mechanism 100, the treatment/fiducial indicator 712 could be configured as to deactuate the treatment tool (such as a surgical scalpel) if it is determined to be in an unsuitable position.

Certain embodiments of the treatment limiter mechanism 100, with the relative positioning determiner, can be configured as a virtual mechanism (which may be actuated and/or controlled based at least in part on the fiducial position associators 710 and/or the treatment/fiducial indicators 712 as described with respect to FIG. 7). As such, certain embodiments of treatment tools can be actuated (either positively or negatively) when positioned in proximity to certain regions or locations of the individual's body. For example, if the treatment tool was positioned close to an undesired or unplanned region on the individual's body, a warning buzzer or alert may appear either within the medical tool and/or from an associated indicator or device. Certain embodiments of the treatment limiter mechanism 100 can be associated with a variety of treatment/fiducial indicators 712, which may be, but are not limited to: display-based, optical-based, audio-based, touch-based, and in certain instances a small (non-harmful) shock may even be provided to a person attempting to position the treatment tool at an undesired or harmful location. Similarly, an optical warning or alarm may also be provided on a portion of the treatment tool (e.g., a scalpel), or some associated display location nearby the individual 102 and/or treating person or process which may be viewed by at least the treating person. FIG. 7 shows one embodiment of the imaging mechanism that can be configured to detect position(s) of the treatment tools as well as the body part(s) of the individual 102 being treated.

Figure 8:
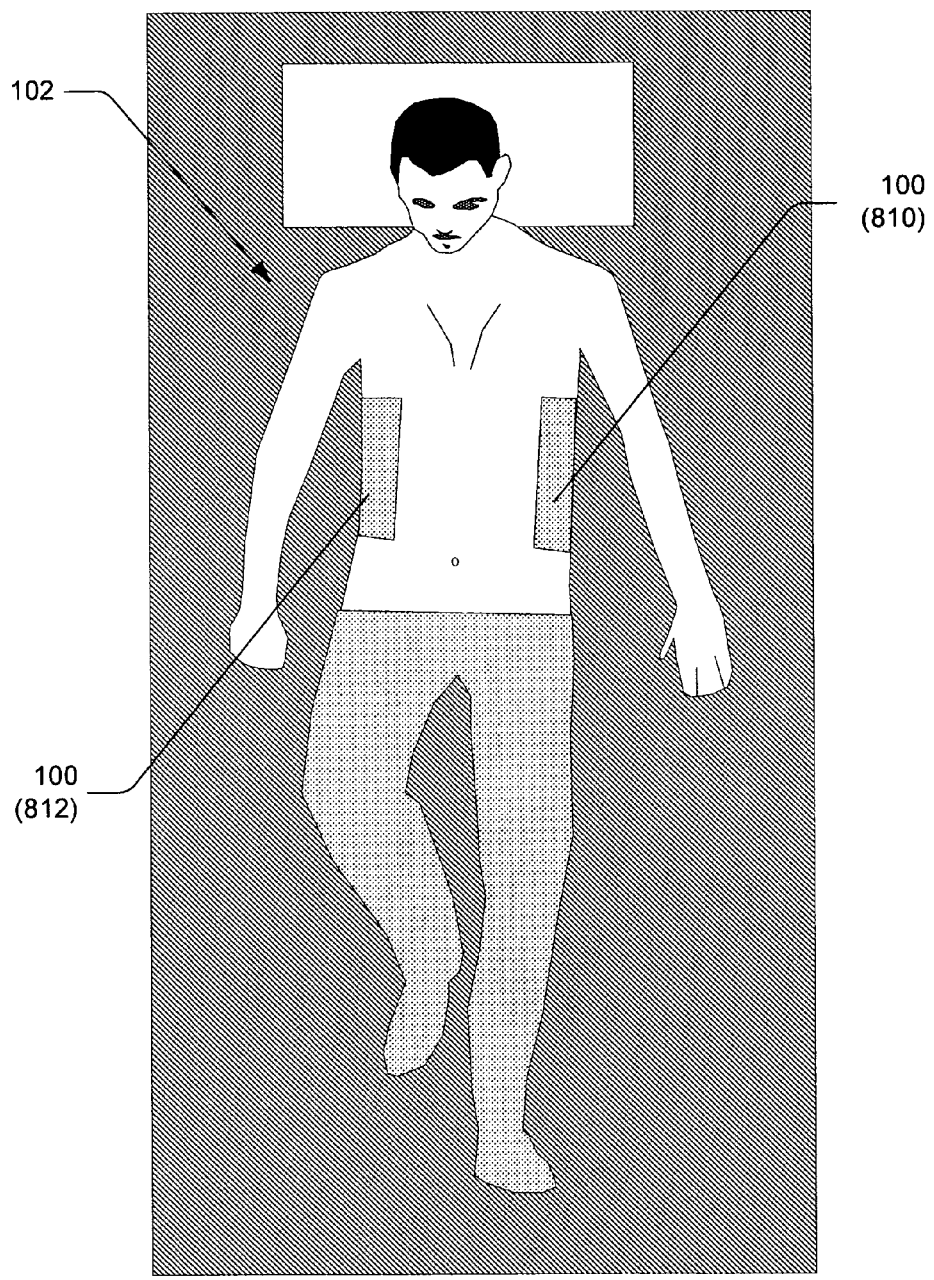
FIG. 8 is a diagram of still another embodiment of the treatment limiter mechanism.

FIG. 8 shows another embodiment of the treatment limiter mechanism 100 that can be configured as to include a reactive region marker. With certain embodiments of the treatment limiter mechanism 100, a locative site can be configured to indicate where not to treat can be marked with the reactive region marker 810. The individual 102 can then be positioned in a desired position(s). Thereupon, a treatment site 812 can be prepared utilizing known sterilizing agents (e.g., prep solution). Thereupon, if the sterilizing agents does or does not (depending on the embodiment) mix with the reactive region marker, there is an indication of a positive indicator or a negative indicator such that the individual respectively could or could not be treated at that location. Certain embodiments of the go indicator can include, but is not limited to, a color change of the sterilizing agent(s) when mixed directly with the locative marker. Such color change of the sterilizing agents can be provided as a signal being provided by a suitable imager and/or color camera monitoring the patient, etc.

Figure 9:
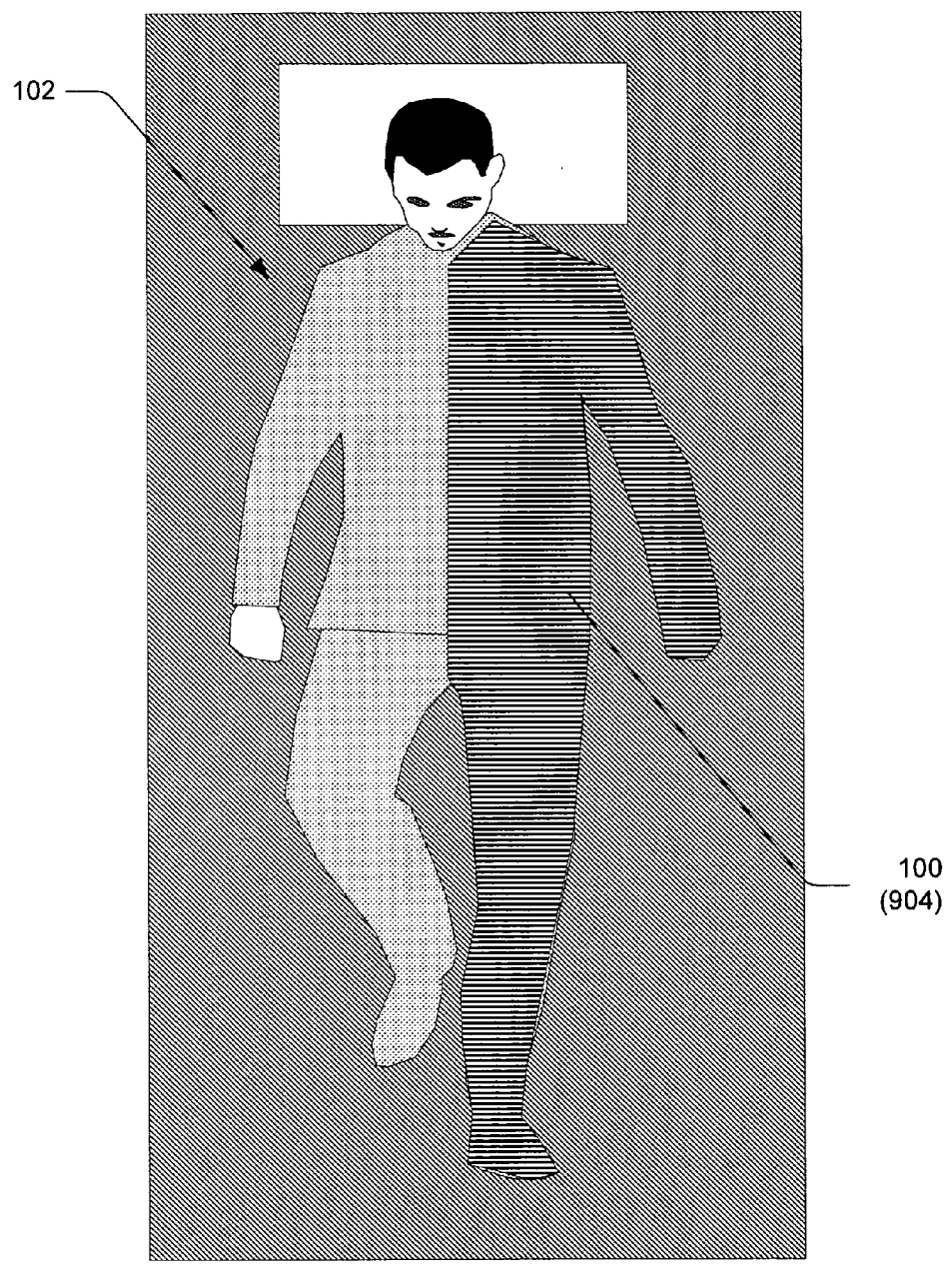
FIG. 9 is a diagram of still another embodiment of the treatment limiter mechanism.

FIG. 9 shows another embodiment of the treatment limiter mechanism 100 that can be configured as a dynamic barrier 904. Certain embodiments of the material at least partially forming the dynamic barrier 904 relative to the treatment limiter mechanism 100 can be layered, coated, and/or provided on a substrate or by itself, and certain portions such as those that are associated with regions of the individual that may or may not be treated may, for example, include a magnetorheologic fluid or similar material. Magnetorheologic fluids are generally understood to change hardness characteristics upon the application (or lack thereof) of either an electric current, electric voltage, and/or electromagnetic fluid. As such, certain embodiments of the dynamic barrier can be configured to change hardness characteristics upon locating the treatment tool either in an area that should be treated, or alternately in an area that should not be treated. For example, the clothing covering the entire left side of the individual's body in FIG. 8, excepting the head, has been covered by the portion of the treatment limiter mechanism 100 covered by the magnetorheologic fluid, which upon actuation or deactuation can become hard, for example. In certain instances, the actuation or deactuation may occur when a surgical tool is positioned in close proximity to a portion of the individual. With certain embodiments of the treatment limiter mechanism 100 which are partially coated with the magnetorheologic fluid, the remainder of the clothing covering his right side can be removed during treatment such as by cutting, etc., and thereby does not form the dynamic barrier whose state may vary upon actuation or deactuation.

Certain embodiments of the dynamic barrier that is situated at an undesired treatment location can thereby be configured to harden if contacted, or come in close proximity by, the treatment tools, etc. By comparison, certain embodiments of the dynamic barrier 904 can be configured to remain relatively soft and/or impregnable if contacted by the treatment tool that is situated at a desired or planned treatment location. As such, certain embodiments of the reactive skin marker can be positioned on a body part that is not desired to be treated. In those instances where the treating person or process is treating the correct side or body part of the individual 102, for example, the dynamic barrier 904 will remain cuttable, and that portion could be easily cut through, removed, and/or accessed using the treatment tool to provide the suitable or planned treatment. In those instances where the treating person or process is treating the incorrect or planned side or body part of the individual 102, the dynamic barrier may harden or stiffen, and that portion of the treatment limiter mechanism will be difficult to cut through, remove, and/or access to limit applying the treatment tool, etc. from providing unsuitable or unplanned treatment. Certain embodiments of the dynamic barrier 904 may be configured to be made of a resinous or other phase-changing material that can change its phase relatively quickly based at least in part on the treatment provided.

Certain embodiments of the treatment limiter mechanism 100, as described in this disclosure, can be configured with an internal position indicator such as a display that may be configurable to indicate an internal position and/or condition of at least a portion of the individual 102 (e.g., which may be direct at, but is not limited to: an internal condition, illness, and/or injury of at least one internal body element, organ, bone, etc.]. Consider that certain embodiments of the treatment limiter mechanism 100 can provide a display with either a representation (e.g., drawing) or an image of an internal portion of the individual 102. Such displays 404 as may be provided by certain embodiments of the treatment limiter mechanism 100 can be used by the treating person or process to explain a treatment, operation, or procedure to the individual 102, or a person associated with the individual.

Certain other embodiments of the treatment limiter mechanism 100 can be configured to largely utilize a chemical reaction such as to display those regions or locations of the individual 102 that should or have been planned to be treated as compared to those regions or locations of the individual 102 that should not or have not been planned to be treated.

There can be a variety of control mechanisms which may be utilized or actuated to control certain embodiments of the treatment limiter mechanism 100. Certain embodiments of the control mechanisms may be a part of, and alternate to, or in addition to certain embodiments of the treatment limiter controller 97 as described in this disclosure with respect to FIG. 2. Certain embodiments of the treatment limiter controller 97 may thereby utilize a variety of hardware, software, mechanical, electromechanical, electronic, mote, other similar, suitable, or known aspects, or combinations of these aspects, such as may be described in this disclosure. Also, such alternatives and/or modifications to the treatment limiter mechanism 100 and/or the treatment limiter controller 97 such as would be known by those skilled in the controller, computer, mote, or other associated art. A variety of adaptive treatment techniques may be utilized to limit treatment as desired or planned, as described in this disclosure. One aspect of motes that makes them suitable for such applications as the treatment limiter mechanism 100 and/or the treatment limiter controller 97 is the ability to disperse them in sufficient numbers (and at relatively low costs) such as to include a sensor, an actuator, and/or an indicator or display such as could be used to indicate to the treating person or process where to treat the individual 102 and/or where not to treat the individual.

Certain embodiments of the treatment limiter mechanism 100 can be highly adaptive to the treatment, the individual 102, and/or the treating person or process; and may utilize prototyping techniques (certain embodiments of which may be relatively rapid to implement) to thereby limit treatment to the individual 102 to planned and/or desired treatment. Alternatively and or additionally to the foregoing, certain embodiments of the treatment limiter mechanism 100 can be configured and/or associated, at least partially, with suitable, inflatable/deflateable, and/or customized pillows or cutouts in bed, such as to limit treatment to desired and/or planned locations.

Certain embodiments of the treatment limiter mechanism 100 can be configured to limit operations, procedures, or other activities to areas where treatment should not be performed. Certain embodiments of the treatment limiter mechanism 100, as described with respect to FIG. 1, could be physically configured to closely fit the individual 102 such as an item of clothing, such as a bodysuit, stocking portion, wrap, bandage, tape, etc. Certain embodiments of the treatment limiter mechanism 100 that are configured to loosely fit the individual 102 may act as a reminder to the treating person to generally treat certain areas (e.g., operate on the right side, not the left side, etc.). Though such differentiations between left and right may appear straight forward to treating persons, and typically are, there are certain instances where the individual 102 may be often rearranged, repositioned, shifted, transitioned, etc., where such treating person(s) or process(es) as doctors, dentists, etc. could reasonably make errors about general locations to operate at; locations of bones, organs, etc.; or particular teeth to work on, etc. Additionally, certain individuals being treated would appreciate the consistency between their planned treatment as indicted or explained to them, and the treatment as indicated by certain embodiments of the treatment limiter mechanism 100. By comparison, certain closely contoured embodiments of the treatment limiter mechanism 100 such as may involve tapes, adhesively-held elements, and the like can be configured with little potential motion between the individual 102 and the treatment limiter mechanism such as to indicate to such treating person(s) as the physician, dentist, veterinarian, etc. to precisely illustrate the desired or planned location of the treatment (such as limiting the application of the treatment to an unsuitable location).

Figure 10:
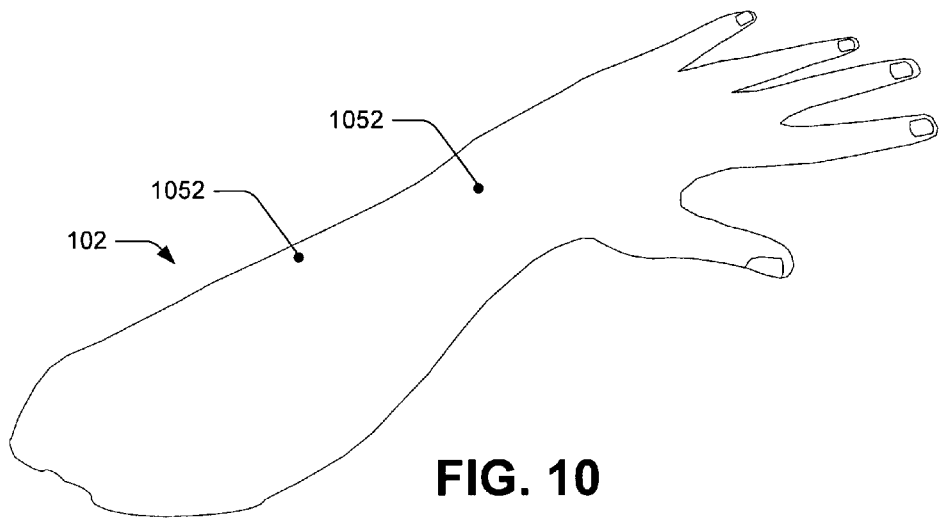
FIG. 10 shows an embodiment of a body part to which one embodiment of the treatment limiter mechanism is to be applied.
Figure 11:
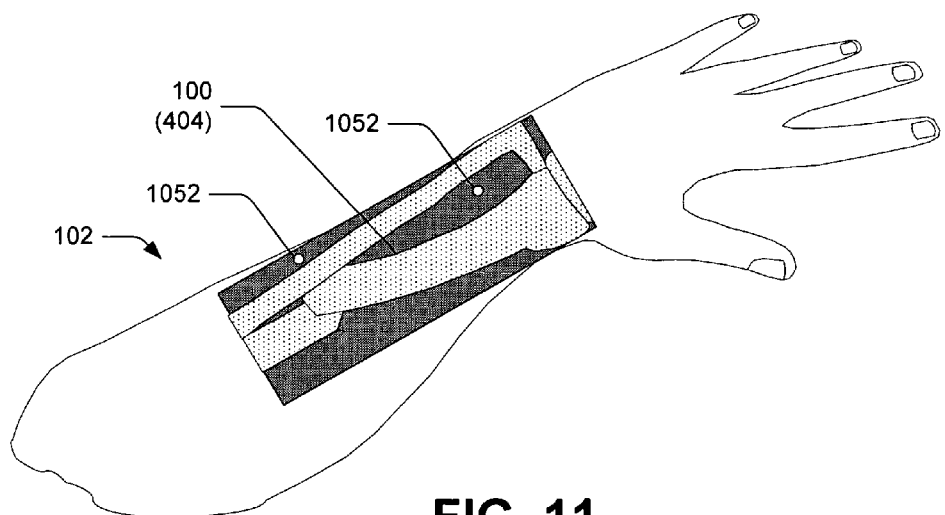
FIG. 11 shows the embodiment of the body part of FIG. 10, with an embodiment of the treatment limiter mechanism being applied thereto.

Additionally, certain embodiments of the treatment limiter mechanism 100 can be configured to illustrate locations of bones, internal organs, at least partially internal parts of the body, etc. such as can be used to indicate the desired location of the treatment, or the condition of the at least partially internal parts of the body such as described with respect to FIGS. 10 and 11. The technique by which the at least partially internal part(s) of the body can be derived can include real-time, recurring, one-time, or other imaging or representation techniques. Certain embodiments of the display 404 of the treatment limiter mechanism 100 can utilize a variety of technologies to produce an image or representation that can include, but not limited to: electromagnetic radiation, ultrasound, computed tomography, fluoroscope, x-rays, electro-optic imaging, electromagnetic imaging, magnetic resonance imaging, etc.

Certain embodiments of the treatment limiter mechanism 100 can also be associated with the treatment of the individual 102 in a variety of different ways with those described in this disclosure intending to be illustrative in nature and not limiting in scope. Certain embodiments of the treatment limiter mechanism 100 can be used by the person(s) or process(es), among others, to enhance the confidence of the individual 102 being treated (and/or their friends or family) that the treatment is indeed well thought out, as well as indicating that the person(s) or process(es) will not treat the individual 102 at an undesired or unplanned location.

Consider the added confidence of a potential individual 102 undergoing a treatment who is wearing certain embodiments of the treatment limiter mechanism 100 that indicates that, for example, the desired or planned treatment is being performed at the correct location, the desired or planned tooth is being pulled by a dentist, the desired or correct body part is being treated by a veterinarian, etc. Certain embodiments of the treatment limiter mechanism 100 can thereby indicate that the treating person(s) is indeed organized, and will presumably more likely perform the desired procedure (or conversely less likely make an error on the treatment or the location of the treatment). Consider that with certain treatments, the individual 102 may be unconscious, and/or otherwise unable or unwilling to communicate with at least some of the treating person(s) or process(es), and/or may be remote from the treating person(s) or process(es) during the treatment.

Certain embodiments of the treatment limiter mechanism 100 can thereby be configured to improve communications and/or understanding between the individual 102 (and/or those associated with the individual) and the treating person(s) relative to the treatment. As such, certain embodiments of the treatment limiter mechanism 100 can be considered as to, and would in actuality be likely to, improve the "bedside manner" of the treating person(s) relative to the individual 102. It is likely that those individuals who experience certain embodiments of the treatment limiter mechanism 100 with certain treating person(s) may likely demand other treatment limiter mechanism(s) be used by subsequent treating persons in associated or unrelated treatments. It is also likely that hospitals, clinics, dentists, veterinarians, other treatment locations, insurance providers, certifying authorities, and the like may require certain embodiments of the treatment limiter mechanism may be used.

With certain treatments and/or certain individuals, the individuals may be uncertain as to what is involved with a particular operation. For instance, certain physicians may select not to display such information as an image such as an x-ray to the individual 102. Alternately, certain individuals may be unable to "translate" an image taken for treatment that is not "located" relative to their body into a location of their own body, for example; and therefore certain embodiments of the treatment limiter mechanism may clarify the injury, illness, treatment, and/or location to the individual. Certain embodiments of the treatment limiter mechanism 100 can thereby be utilized by the individual 102 to indicate more precisely where an illness, injury, or other malady may be situated, and thereby allow the individual 102 to gain a greater understanding of their own illness or injury.

In certain instances, a detected injury, illness, or malady by the treating person(s) may not match up with that as understood by the individual 102. For instance, after a treating person indicates to the individual being treated where they are intending to treat, the treating person may note that pain or symptoms are not originating from the treated location. By being able to illustrate to the individual 102 where the treating person or process is to treat, the individual can provide input as to whether the treating person or process is at the correct location. There may be a number of reasons why what the individual feels or believes may be appropriate treatment may not confirm to a treating person's or processes' suggested treatment. For example, the individual 102 may sense pain at a particular location (e.g., referred pain), while the actual injury or illness may be located elsewhere. Alternatively, it is possible the treating person or process may misdiagnose and/or misunderstand the illness or injury. Certain embodiments of the treatment limiting mechanism may be particularly suited to those instances where the interpretation of the treatment by the individual does not match their feelings. For instance, if a dentist or doctor is providing treatment to the right side of the individual as indicated by the treatment limiter mechanism, while their pain is in their left side, then the individual would question the treating person as to potentially avert an unsuitable treatment, or more closely understand a proper treatment. It appears likely that making the individual 102 more aware of the scope and location of a planned treatment could be used to considerably inspire confidence by a number of individuals with respect to the treating person and/or the treatment.

Certain embodiments of the treatment limiter mechanism 100, as described with respect to FIGS. 5 and/or 11, can include the display 404 that can be positioned [e.g., secured, taped, worn] relative an exposed surface of the individual 102 such as to provide the display 404 of the individual, or a portion thereof, that is undergoing treatment. Certain embodiments of the treatment limiter mechanism may include the display 404, while others may not. Certain embodiments of the display 404 may be selected depending largely on how much the displayed body part, bone, bone fragment, organ, condition, etc. can change over time. Certain embodiments of the display 404 can be performed in real time, similar to as described with respect to FIG. 5 in which a display or monitor of the individual may be included that can be observed by the treating person. Certain embodiments of the display 404 as described with respect to FIG. 11 can include an x-ray, scan, MRI, or other image and/or information relating to the individual, the treatment, the treating person, etc. that can be taped, secured, affixed, and/or otherwise secured to the individual. Associated with the display are one or more position identifying mark(s) 1052 that may be provided on the individual prior to the scan, x-ray, MRI, etc., which will pick up the presence of the position identifying mark(s). As such, the display 404 can be positioned on the individual in a manner that corresponds with the position identifying mark(s) 1052, thereby causing the positioning of the display to correspond to the position of the individual.

Certain embodiments of the display 404 that are movable may be more suited for treatment of the individual for conditions or states, etc. that can change over time. Consider, for example, that a display as to a current state or condition of a heart during heart surgery would be expected to have more relevance if displayed on a real-time or continually updated basis as, for example, a broken bone that would likely not move. The type of treatment as well as the areas, regions, bones, organs, and/or body parts being treated, as well as the type of individual, would largely factor into what a desirable type of imaging or photography that may be associated with the display 404 for the treatment limiter mechanism.

Figure 12:
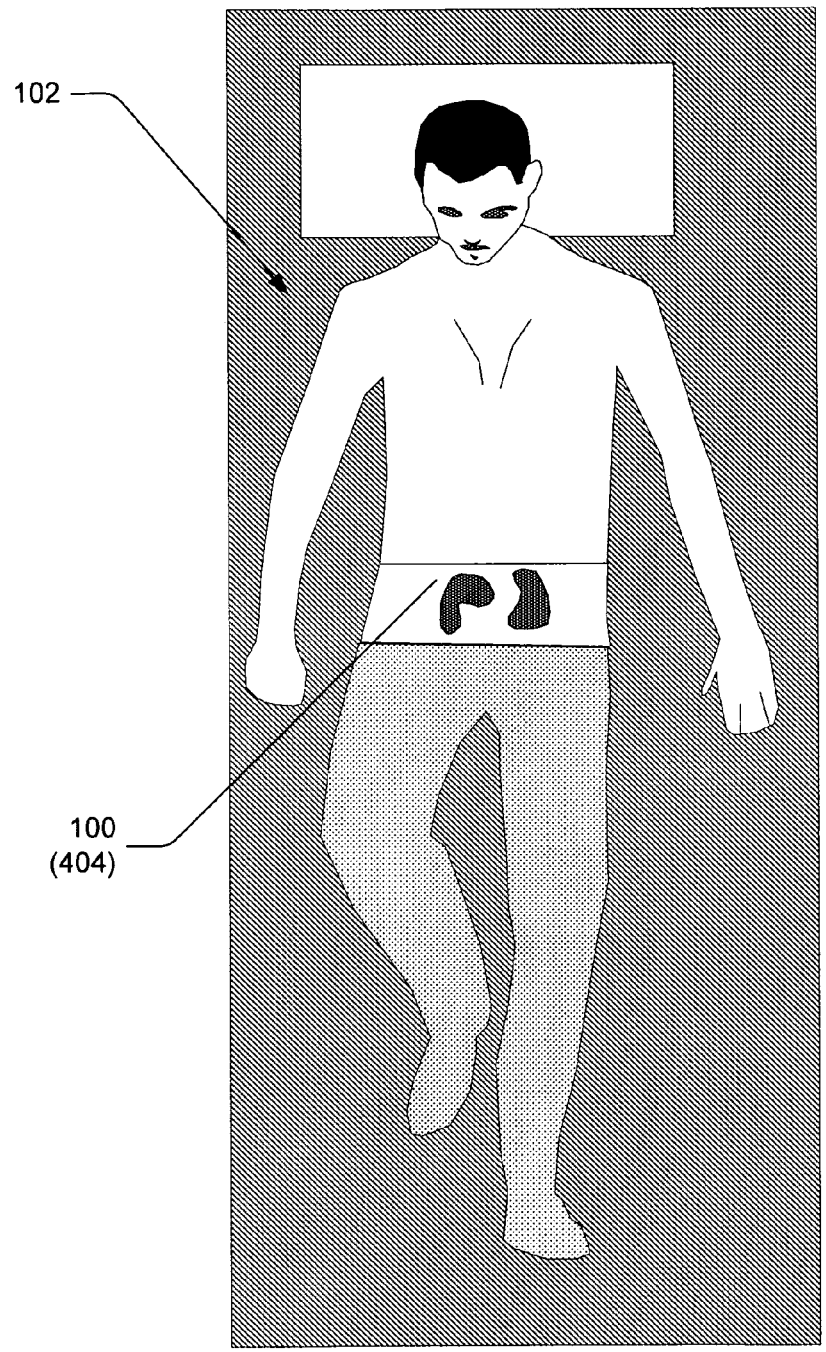
FIG. 12 is a diagram of still another embodiment of the treatment limiter mechanism including a display.

FIG. 12 shows another embodiment of the display 404 that are configured to be worn as an item of clothing. For instance, assure the individual 102 is undergoing kidney surgery or treatment, it may be desired to show the location of the outline of the particular organ, bone, body part, etc. prior to treatment. Consider that with certain kidney surgery, for example, there may be confusion between the left and right kidneys, as to which one to treat and/or operate on (e.g., resect). Certain embodiments of the display or pixel elements which at least partially form the treatment limiter mechanism 100 may be integrated in the fabric of the clothing (not shown). Certain embodiments of the display or pixel elements associated with the display 404 can include, but are not limited to, LEDs, LCDs, diode displays, mote-display elements, monochromatic displays, multichromatic displays, etc. The density of the display or pixel elements of the display 404 can be selected based on such factors as desired clarity, type of treatment, preferences of treating person, etc. Certain automated or robotic embodiments of the treatment limiter 100 can rely, for example, on more or less precise images of the organ, bone, body part, etc.

2. Certain Embodiments of the Treatment Limiter Controller

Figure 2:
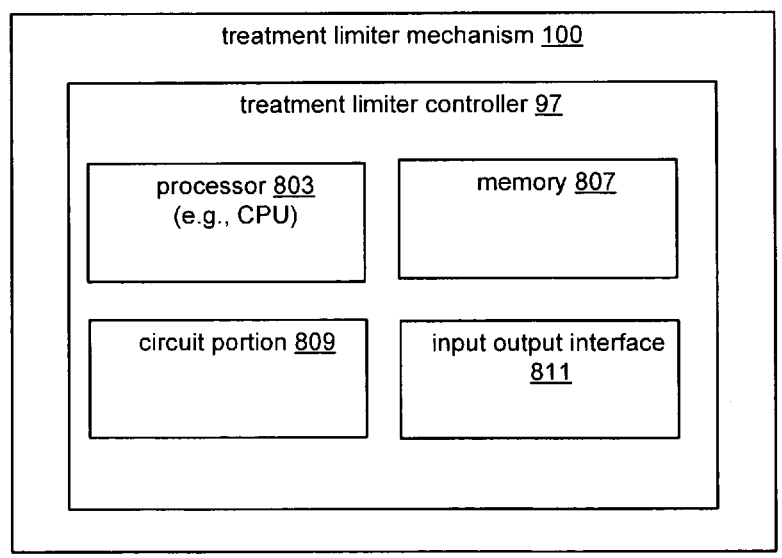
FIG. 2 is a block diagram of one embodiment of the treatment limiter mechanism, including a treatment limiter controller.

This disclosure describes a number of embodiments of the treatment limiter controller 97 as described with respect to FIG. 2, which are intended to control operations of the treatment limiter mechanism 100. A considerable number of the treatment limiter mechanism 100 as described in this disclosure can utilize a number of embodiments of the treatment limiter controller 97 to determine whether the treatment tool is being positioned nearby an area or region that is intended or planned to be treated, or not. Certain embodiments of the treatment limiter mechanism 100 can include the treatment limiter controller 97; while other embodiments of the treatment limiter mechanism may not include utilizing certain embodiments of the treatment limiter controller. For instance, certain embodiments of the treatment limiter mechanism 100 including the treatment limiter controller 97, certain embodiments of which can be largely microprocessor-based, and can provide for largely automated operation or assembly of the treatment limiter mechanism 100. By comparison, certain embodiments of the treatment limiter mechanism 100 as described in this disclosure can be operated utilizing largely mechanical-based and/or manual techniques, and may not utilize the treatment limiter controller 97. FIG. 2 thereby shows a block diagram of certain embodiments of the treatment limiter mechanism 100 that can include the treatment limiter controller 97 such as are either at least partially automated, and/or at least partially are controlled by the treatment limiter mechanism. Certain embodiments of the treatment limiter controller 97 can be configured to be automated and/or operated at least partially using robotics, for example.

Certain embodiments of the treatment limiter mechanism 100 thereby can include, but is not limited to, any particular configuration of the treatment limiter controller 97. Certain embodiments of the treatment limiter controller 97 can be computer based, controller based, mote based, cellular telephone-based, and/or electronics based. Certain embodiments of the treatment limiter controller 97 can be segmented into modules or network nodes such as to be distributed across the individual; and may utilize a variety of wireless communications and/or networking technologies to allow information, data, etc. to be transferred to the various distinct portions or embodiments to perform, a variety of operations associated with of the treatment limiter mechanism 100. Certain embodiments of the treatment limiter controller 97 can be configured as a unitary or stand alone device.

Certain embodiments of the treatment limiter controller 97 can thereby vary as to their level of automation, complexity, and/or sophistication; and can be utilized to control, setup, establish, and/or maintain communications between a number of different portions of the treatment limiter mechanism 100. As described within this disclosure, multiple ones of the different embodiments of the treatment limiter mechanism 100 can transfer information or data relating to the communication link to or from a remote location and/or some intermediate device as might be associated with communication, monitoring and/or other activities.

Certain embodiments of the treatment limiter controller 97, as well as certain embodiments of the treatment limiter mechanism 100 (in general), can utilize distinct firmware, hardware, and/or software technology. For example, mote-based technology, microprocessor-based technology, microcomputer-based technology, general-purpose computer technology, specific-purpose computer technology, Application-Specific Integrated Circuits, and/or a variety of other computer technologies can be utilized for certain embodiments of at least a portion of the treatment limiter controller 97, as well as be included in certain embodiments of the treatment limiter mechanism 100.

Certain embodiments of the treatment limiter controller 97 can as described with respect to FIG. 2 can include a processor 803 such as a central processing unit (CPU), a memory 807, a circuit or circuit portion 809, and an input output interface (I/O) 811 that may include a bus (not shown). Certain embodiments of the treatment limiter controller 97 of the treatment limiter mechanism 100 can include and/or be a portion of a general-purpose computer, a specific-purpose computer, a microprocessor, a microcontroller, a personal display assistant (PDA), a cellular phone, a digital phone, a wireless communicating device, a hard-wired phone, and/or any other known suitable type of communications device, computer, and/or controller that can be implemented in hardware, software, electromechanical devices, and/or firmware. Certain embodiments of the processor 803, as described with respect to FIG. 2, can perform the processing and arithmetic operations for certain embodiments of the treatment limiter controller 97 of the treatment limiter mechanism 100. Certain embodiments of the treatment limiter controller 97 of the treatment limiter mechanism 100 can control the signal processing, database querying and response, computational, timing, data transfer, and other processes associated with certain embodiments of the treatment limiter controller 97 of the treatment limiter mechanism 100.

Certain embodiments of the memory 807 of the treatment limiter controller 97 can include a random access memory (RAM) and/or read only memory (ROM) that together can store the computer programs, operands, and other parameters that control the operation of certain embodiments of the treatment limiter controller 97 of the treatment limiter mechanism 100. The memory 807 can be configurable to contain information obtained, retained, or captured by that particular treatment limiter controller 97 of the treatment limiter mechanism 100.

Certain embodiments of the bus can be configurable to provide for digital information transmissions between the processor 803, circuits 809, memory 807, I/O 811, and/or the image memory or storage device (which may be integrated or removable). In this disclosure, the memory 807 can be configurable as RAM, flash memory, semiconductor-based memory, of any other type of memory that can be configurable to store data pertaining to images and/or other information that could be used with certain embodiments of the treatment limiter mechanism 100. The bus also connects I/O 811 to the portions of certain embodiments of the treatment limiter controller 97 of either the treatment limiter mechanism 100 that can either receive digital information from, or transmit digital information to other portions of the treatment limiter mechanism 100, or other systems and/or networking components associated with.

Certain embodiments of the treatment limiter controller 97 of the treatment limiter mechanism 100, as described with respect to FIG. 2, can include a transmitter portion (not shown) that can be either included as a portion of certain embodiments of the treatment limiter controller 97 of the treatment limiter mechanism 100. Certain embodiments of the treatment limiter controller 97 can alternately be provided as a separate unit (e.g., microprocessor-based). In certain embodiments, the transmitter portion can transmit image information between certain embodiments of the treatment limiter controller 97 of the treatment limiter mechanism 100. Certain embodiments of the treatment limiter controller 97 of the treatment limiter mechanism 100 as described with respect to FIG. 2 can include an operation altering portion (not shown) that can be either included as a portion of certain embodiments of the treatment limiter controller 97 of the treatment limiter mechanism 100, or alternately can be provided as a separate unit (e.g., microprocessor-based).

Certain embodiments of the memory 807 can provide one example of a memory storage portion. In certain embodiments, the monitored value includes but is not limited to: a percentage of the memory 807, an indication of data that is or can be stored in the memory 807, or for data storage or recording interval. To provide for overflow ability for the memory 807 of certain embodiments of the treatment limiter controller 97 of the treatment limiter mechanism 100, a secondary storage device can be operably coupled to the memory 807 to allow a controllable transmitting of data, information, and/or images between certain embodiments of the treatment limiter controller 97 of the treatment limiter mechanism 100.

In certain embodiments, a secondary communication link can be established between the certain embodiments of the treatment limiter controller 97 of the treatment limiter mechanism 100. The secondary communication link can be structured in a similar manner as, or indeed act as, a communication link; or alternatively can utilize network-based computer connections, Internet connections, etc. to provide information and/or data transfer between certain embodiments of the treatment limiter controller 97 of the treatment limiter mechanism 100.

In certain embodiments of the treatment limiter controller 97 of the treatment limiter mechanism 100, the particular elements of certain embodiments of the treatment limiter controller 97 of the treatment limiter mechanism 100 (e.g., the processor 803, the memory 807, the circuits 809, and/or the I/O 811) can provide a monitoring function to convert raw data as displayed by an indicator. A monitoring function as provided by certain embodiments of the treatment limiter controller 97 of the treatment limiter mechanism 100 can be compared to a prescribed limit, such as whether the number of images contained in the memory 807, the amount of data contained within the memory 807, or some other measure relating to the memory is approaching some value. The limits to the value can, in different embodiments, be controlled by the user or the manufacturer of certain embodiments of the treatment limiter controller 97 of the treatment limiter mechanism 100. In certain embodiments, the memory 807 can store but should not be limited to such information as: data, information, displayable information, readable text, motion images, video images, and/or audio images, etc.

In certain embodiments, the I/O 811 provides an interface to control the transmissions of digital information between each of the components in certain embodiments of the treatment limiter controller 97 of the treatment limiter mechanism 100. The I/O 811 also provides an interface between the components of certain embodiments of the treatment limiter controller 97 of the treatment limiter mechanism 100. The circuits 809 can include such other user interface devices as a display and/or a keyboard. In other embodiments, the treatment limiter controller 97 of the treatment limiter mechanism 100 can be constructed as a specific-purpose computer such as an application-specific integrated circuit (ASIC), a microprocessor, a microcomputer, or other similar devices.

As such, various embodiments of the treatment limiter mechanism 100 and/or the treatment limiter controller 97 can be configured utilizing relatively complex or simple computer and/or controller technology. As computer and/or controller technology evolves, it is intended that certain embodiments of the treatment limiter mechanism 100 and/or the treatment limiter controller 97 can be modified or adapted to utilize the modifying technology.

3. Certain Embodiments of Logic Associated with the Treatment Limiter Mechanism, the Treatment Limiter Controller, and Relevant Flowcharts Within the disclosure, flow charts of the type described in this disclosure apply to method steps as performed by a computer or controller. The flow charts can also apply to apparatus devices, such as an antenna or a node associated therewith that can include, e.g., a general-purpose computer or specialized-purpose computer whose structure along with the software, firmware, electro-mechanical devices, and/or hardware, can perform the process or technique described in the flow chart.

Figure 13:
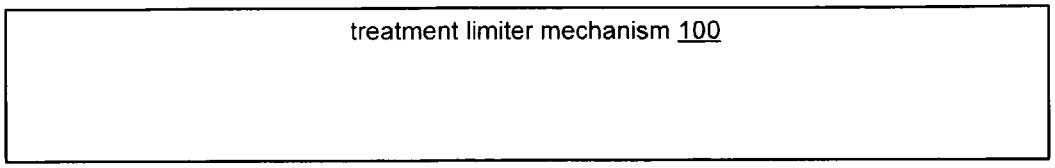
FIG. 13 shows another embodiment of the treatment limiter mechanism.

FIG. 13 shows one embodiment of a treatment limiter technique as can be performed with a variety of embodiments of the treatment limiter mechanism 100, as described in this disclosure with respect to FIGS. 1 to 12, for example. Certain embodiments of the treatment limiter mechanism 100 can be configured to limit treatment to prescribed regions of an individual based at least in part on positioning the treatment limiter mechanism relative to the individual at least partially allowing treating at least some desired or planned location that is desired or planned to be treated. Certain embodiments of the treatment limiter mechanism can be configured to allow treating other locations that are not planned or not desired to be treated from being treated.

Figure 14A:
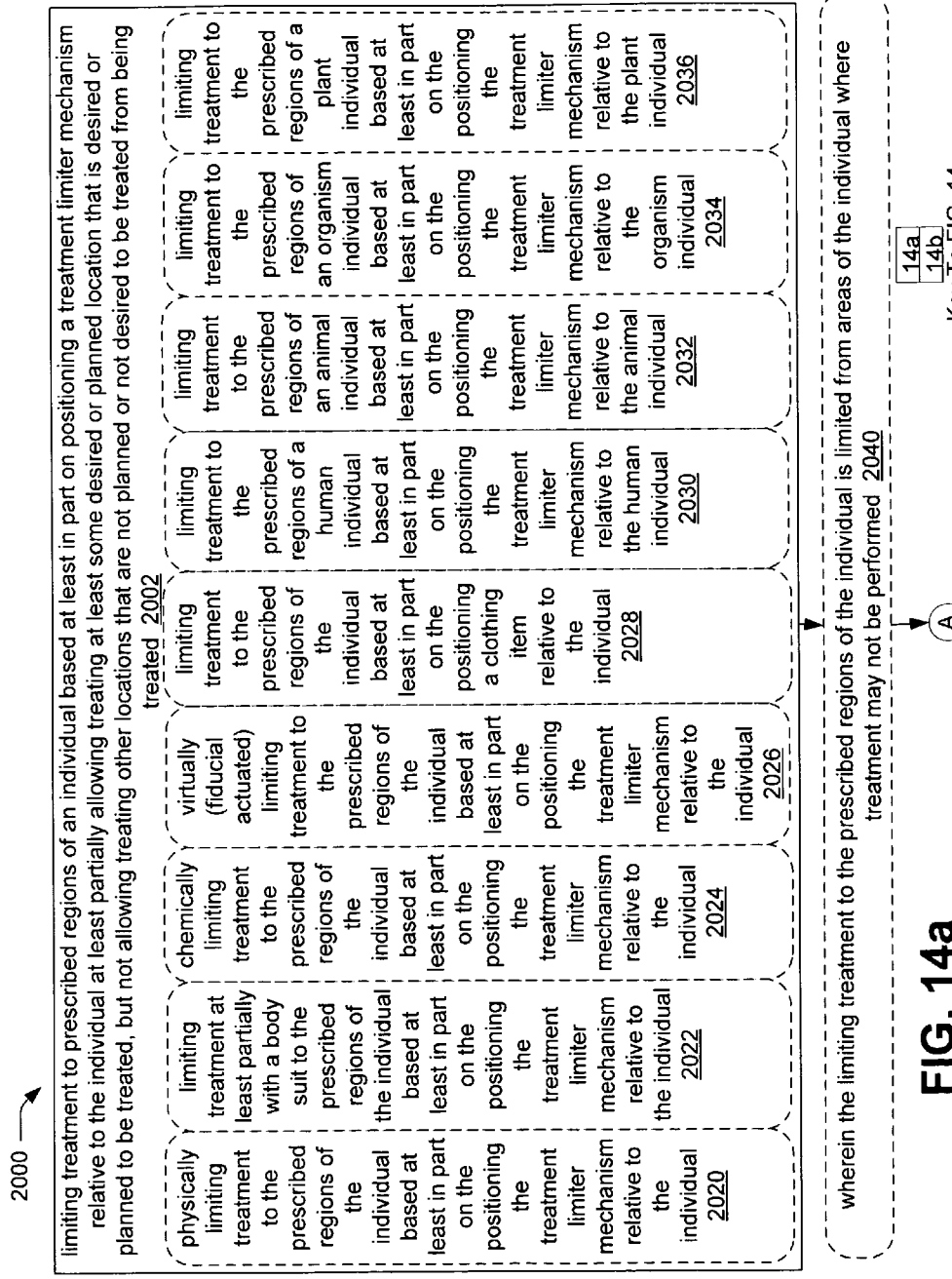
FIG. 14 (including FIGS. 14a and 14b) shows a flow chart of an embodiment of the treatment limiter mechanism as described with respect to FIG. 13.
Figure 14B:
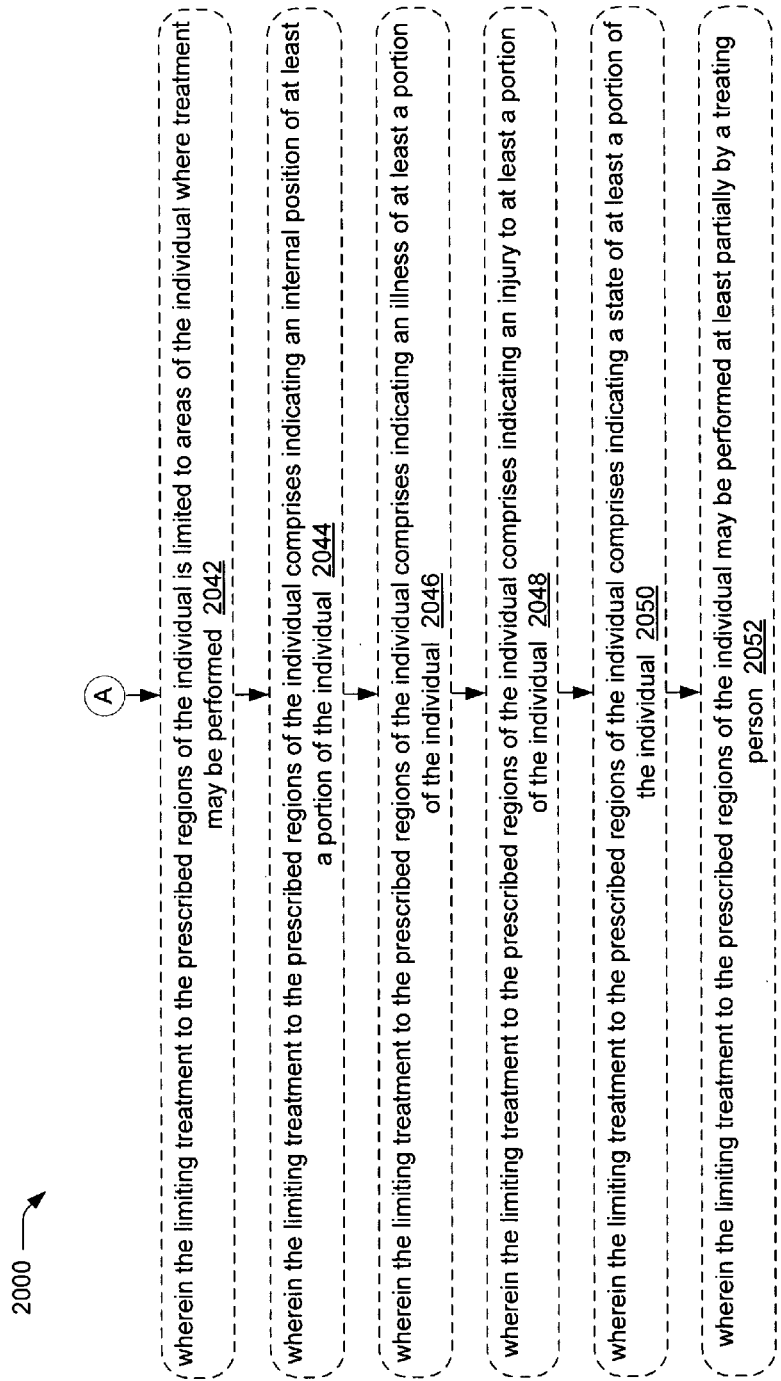

One embodiment of a high-level flowchart of a treatment limiter technique 2000 as described with respect to FIG. 14 (including FIGS. 14a and 14b) and can include, but is not limited to, operation 2002, and optional operations 2040, 2042, 2044, 2046, 2048, 2050, and/or 2052. One embodiment of operation 2002 can include, but is not limited to, operations 2020, 2022, 2024, 2026, 2028, 2030, 2032, 2034, and/or 2036. The high-level flowchart of FIG. 14 (including FIGS. 14a and 14b) should be considered in combination with the embodiments of the treatment limiter mechanism 100, as described with respect to FIG. 13. One embodiment of operation 2002 can include, but is not limited to, limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated. For example, certain embodiments of the limiting treatment, as described in this disclosure, can be configured to limit treatment to prescribed regions of an individual based at least in part on allowing treating at least some desired or planned location that is desired or planned to be treated. Also for example, certain embodiments of the treatment limiter mechanism can be configured to allow treating other locations that are not planned or not desired to be treated from being treated. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2020, that can include, but is not limited to, physically limiting treatment to the prescribed regions of the individual based at least in part on the positioning the treatment limiter mechanism relative to the individual. For example, certain embodiments of the limiting treatment, as described in this disclosure, can be physically limited to the prescribed regions. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2022, that can include, but is not limited to, limiting treatment at least partially with a body suit to the prescribed regions of the individual based at least in part on the positioning the treatment limiter mechanism relative to the individual. For example, certain embodiments of the limiting treatment can utilize a body suit. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2024, that can include, but is not limited to, chemically limiting treatment to the prescribed regions of the individual based at least in part on the positioning the treatment limiter mechanism relative to the individual. For example, certain embodiments of the limiting treatment as described in this disclosure can involve chemically changing to limit treatment, such as utilizing magnetorheologic fluid that can change hardnesss by the application of electric fields, or alternately utilizing reactive skin markers as described in this disclosure. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2026, that can include, but is not limited to, virtually limiting treatment to the prescribed regions of the individual based at least in part on the positioning the treatment limiter mechanism relative to the individual. For example, certain embodiments of the limiting treatment, as described in this disclosure, can be virtually actuated such as to include fiducial devices, such as described with respect to FIG. 7. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2028, that can include, but is not limited to, limiting treatment to the prescribed regions of the individual based at least in part on the positioning a clothing item relative to the individual. For example, certain embodiments of the limiting treatment, as described in this disclosure, can be configured as clothing. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2030, that can include, but is not limited to, limiting treatment to the prescribed regions of a human individual based at least in part on the positioning the treatment limiter mechanism relative to the human individual. For example, certain embodiments of the limiting treatment, as described in this disclosure, can be applied to humans. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2032, that can include, but is not limited to, limiting treatment to the prescribed regions of an animal individual based at least in part on the positioning the treatment limiter mechanism relative to the animal individual. For example, certain embodiments of the limiting treatment, as described in this disclosure, can be applied to animals. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2034, that can include, but is not limited to, limiting treatment to the prescribed regions of an organism individual based at least in part on the positioning the treatment limiter mechanism relative to the organism individual. For example, certain embodiments of the limiting treatment, as described in this disclosure, can be applied to organisms such as to describe particular areas of a culture or field to treat. One embodiment of the limiting treatment to prescribed regions of an individual based at least in part on positioning a treatment limiter mechanism relative to the individual at least partially allowing treating at least some desired or planned location that is desired or planned to be treated, but not allowing treating other locations that are not planned or not desired to be treated from being treated of operation 2002 can include operation 2036, that can include, but is not limited to, limiting treatment to the prescribed regions of a plant individual based at least in part on the positioning the treatment limiter mechanism relative to the plant individual. For example, certain embodiments of the limiting treatment, as described in this disclosure, can be applied to plant individuals. One embodiment of operation 2040 can include, but is not limited to, wherein the limiting treatment to the prescribed regions of the individual is limited from areas of the individual where treatment may not be performed. For example, certain embodiments of the limiting treatment can include limiting those areas that can be treated. One embodiment of operation 2042 can include, but is not limited to, wherein the limiting treatment to the prescribed regions of the individual is limited to areas of the individual where treatment may be performed. For example, certain embodiments of the limiting treatment may include applying the treatment to those areas where treatment may be performed. One embodiment of operation 2044 can include, but is not limited to, wherein the limiting treatment to the prescribed regions of the individual comprises indicating an internal position of at least a portion of the individual. For example, certain embodiments of the limiting treatment may include indicating an internal position of a body part, bone, bone fragment, organ, etc. One embodiment of operation 2046 can include, but is not limited to, wherein the limiting treatment to the prescribed regions of the individual comprises indicating an illness of at least a portion of the individual. For example, certain embodiments of the limiting treatment may include indicating an illness of the individual, or a portion thereof. One embodiment of operation 2048 can include, but is not limited to, wherein the limiting treatment to the prescribed regions of the individual comprises indicating an injury to at least a portion of the individual. For example, certain embodiments of the limiting treatment may include indicating an injury of the individual, or a portion thereof. One embodiment of operation 2050 can include, but is not limited to, wherein the limiting treatment to the prescribed regions of the individual comprises indicating a state of at least a portion of the individual. For example, certain embodiments of the limiting treatment may include indicating a state of the individual, or a portion thereof. One embodiment of operation 2052 can include, but is not limited to, wherein the limiting treatment to the prescribed regions of the individual may be performed at least partially by a treating person. For example, certain embodiments of the limiting treatment may be performed by the treating person such as a physician, a dentist, a veterinarian, an ambulance driver, a ski patrol, a lifeguard, etc. The order of the operations, methods, mechanisms, etc. as described with respect to FIG. 14 (including FIGS. 14a and 14b) is intended to be illustrative in nature, and not limited in scope.

Figure 15:
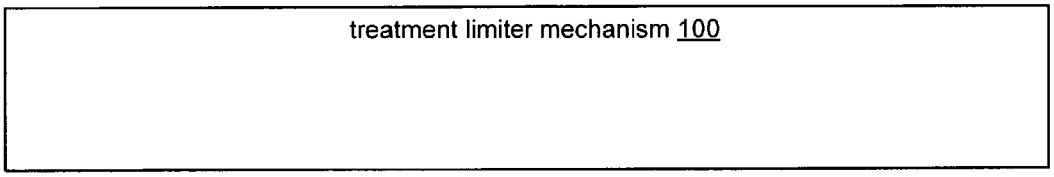
FIG. 15 shows another embodiment of the treatment limiter mechanism.

FIG. 15 shows one embodiment of a treatment limiter technique as can be performed with a variety of embodiments of the treatment limiter mechanism 100, as described in this disclosure with respect to FIGS. 1 to 12. For example, certain treatment limiter mechanisms can indicate a location of a treatment to an individual that may be situated relative to at least a portion of the individual to indicate the location of an at least partially internal portion of the individual.

Figure 16:
FIG. 16 shows a flow chart of an embodiment of the treatment limiter mechanism as described with respect to FIG. 15.

One embodiment of a high-level flowchart of a treatment limiter technique 2100 as described with respect to FIG. 16 and can include, but is not limited to, operation 2102. One embodiment of operation 2102 can include, but is not limited to, operations 2120, 2122, 2124, 2126, and/or 2128. The high-level flowchart of FIG. 16 should be considered in combination with the embodiments of the treatment limiter mechanism 100, as described with respect to FIG. 15. One embodiment of operation 2102 can include, but is not limited to, indicating a location of a treatment to an individual that may be situated relative to at least a portion of the individual to indicate the location of an at least partially internal portion of the individual. For example, indicating the location that is to be treated, or alternately indicating a region that is not to be treated. One embodiment of the indicating a location of a treatment to an individual that may be situated relative to at least a portion of the individual to indicate the location of an at least partially internal portion of the individual of operation 2102 can include operation 2120, that can include, but is not limited to, indicating repetitively the location of the treatment to the individual to be situated relative to the at least the portion of the individual to indicate the location of the at least partially internal portion of the individual. For example, repetitively indicating the location of the treatment to the individual, such as by displaying a moving image indicating a region or area to be treated or alternately not to be treated. One embodiment of the indicating a location of a treatment to an individual that may be situated relative to at least a portion of the individual to indicate the location of an at least partially internal portion of the individual of operation 2102 can include operation 2122, that can include, but is not limited to, indicating on a one-time basis the location of the treatment to the individual to be situated relative to the at least the portion of the individual to indicate the location of the at least partially internal portion of the individual. For example, indicating using a single image of the region or area to be treated and/or not treated. One embodiment of the indicating a location of a treatment to an individual that may be situated relative to at least a portion of the individual to indicate the location of an at least partially internal portion of the individual of operation 2102 can include operation 2124, that can include, but is not limited to, indicating on a real time basis the location of the treatment to the individual to be situated relative to the at least the portion of the individual to indicate the location of the at least partially internal portion of the individual. For example, indicating on a real time basis an area to be treated, or alternately not treated. One embodiment of the indicating a location of a treatment to an individual that may be situated relative to at least a portion of the individual to indicate the location of an at least partially internal portion of the individual of operation 2102 can include operation 2126, that can include, but is not limited to, indicating the location of the treatment to the individual to be situated relative to the at least the portion of the individual to indicate the location of an at least partially internal bone of the individual. For example, indicating an area to be treated relative to a bone of the individual. One embodiment of the indicating a location of a treatment to an individual that may be situated relative to at least a portion of the individual to indicate the location of an at least partially internal portion of the individual of operation 2102 can include operation 2128, that can include, but is not limited to, indicating the location of the treatment to the individual to be situated relative to the at least the portion of the individual to indicate the location of an at least partially internal organ of the individual. For example, indicating an area to be treated relative to an organ of the individual. The order of the operations, methods, mechanisms, etc. as described with respect to FIG. 16 is intended to be illustrative in nature, and not limited in scope.

Figure 17:
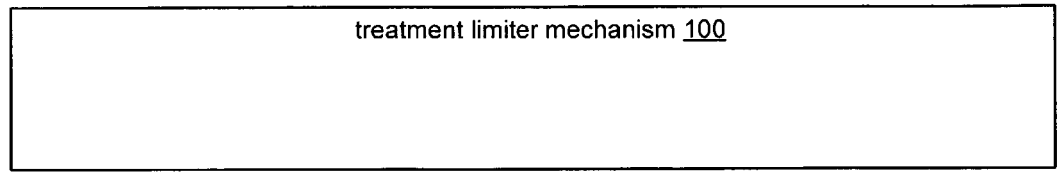
FIG. 17 shows another embodiment of the treatment limiter mechanism.

FIG. 17 shows one embodiment of a treatment limiter technique as can be performed with a variety of embodiments of the treatment limiter mechanism 100, as described in this disclosure with respect to FIGS. 1 to 12. For example, at least a portion of certain embodiments of the treatment limiter mechanisms can be configured at least partially in response to attempting to treat at least a portion of an individual associated with the treatment limiter mechanism.

Figure 18:
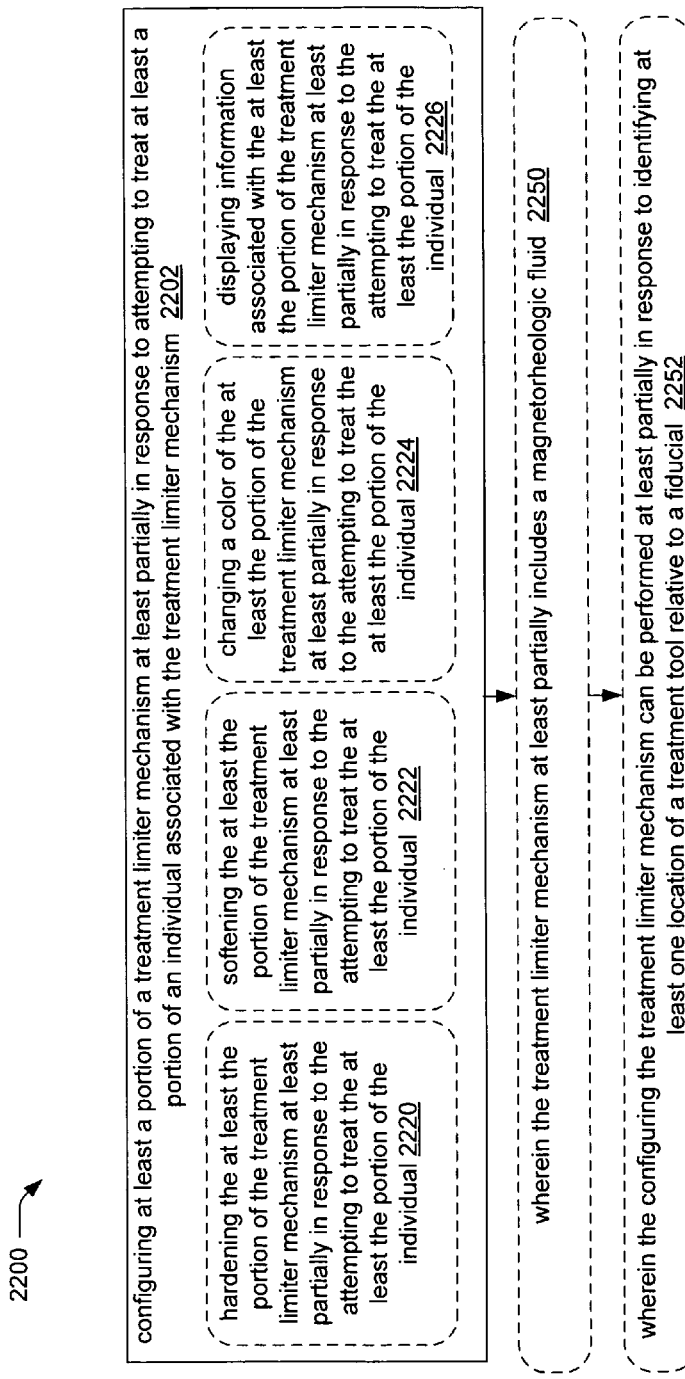
FIG. 18 shows a flow chart of an embodiment of the treatment limiter mechanism as described with respect to FIG. 17.

One embodiment of a high-level flowchart of a treatment limiter technique 2200 as described with respect to FIG. 18 and can include, but is not limited to, operation 2202 and optional operations 2250 and/or 2252. One embodiment of operation 2202 can include, but is not limited to, operations 2220, 2222, 2224, and/or 2226. The high-level flowchart of FIG. 18 should be considered in combination with the embodiments of the treatment limiter mechanism 100, as described with respect to FIG. 17. One embodiment of operation 2202 can include, but is not limited to, configuring at least a portion of a treatment limiter mechanism at least partially in response to attempting to treat at least a portion of an individual associated with the treatment limiter mechanism. For example, configuring the at least the portion of the treatment limiter mechanism such as to limit treatment and/or allow treatment at particular regions, at least partially in response to attempting to treat the portion of the individual which the treatment limiter mechanism is associated with. Certain embodiments of the configuring at least a portion of a treatment limiter mechanism at least partially in response to attempting to treat at least a portion of an individual associated with the treatment limiter mechanism of operation 2202 can include operation 2220 that can include, but is not limited to, hardening the at least the portion of the treatment limiter mechanism at least partially in response to the attempting to treat the at least the portion of the individual. For example, hardening at least a portion of the treatment limiter mechanism at least partially in response to an attempt to treat the at the least the portion of the individual. Certain embodiments of the configuring at least a portion of a treatment limiter mechanism at least partially in response to attempting to treat at least a portion of an individual associated with the treatment limiter mechanism of operation 2202 can include operation 2222 that can include, but is not limited to, softening the at least the portion of the treatment limiter mechanism at least partially in response to the attempting to treat the at least the portion of the individual. For example, softening at least a portion of the treatment limiter mechanism at least partially in response to an attempt to treat the at the least portion of the individual. Certain embodiments of the configuring at least a portion of a treatment limiter mechanism at least partially in response to attempting to treat at least a portion of an individual associated with the treatment limiter mechanism of operation 2202 can include operation 2224 that can include, but is not limited to, changing a color of the at least the portion of the treatment limiter mechanism at least partially in response to the attempting to treat the at least the portion of the individual. For example, changing the color of at least a portion of the treatment limiter mechanism at least partially in response to an attempt to treat the at the least the portion of the individual. Certain embodiments of the configuring at least a portion of a treatment limiter mechanism at least partially in response to attempting to treat at least a portion of an individual associated with the treatment limiter mechanism of operation 2202 can include operation 2226 that can include, but is not limited to, displaying information associated with the at least the portion of the treatment limiter mechanism at least partially in response to the attempting to treat the at least the portion of the individual. For example, displaying information associated with the treatment limiter mechanism at least partially in response to an attempt to treat the at the least the portion of the individual. Certain embodiments of operation 2250 can include, but is not limited to, wherein the treatment limiter mechanism at least partially includes a magnetorheologic fluid. For instance, the treatment limiter mechanism includes, such as being coated or inserted with, the magnetorheologic fluid. Certain embodiments of operation 2252 can include, but is not limited to, wherein the configuring the treatment limiter mechanism can be performed at least partially in response to identifying at least one location of a treatment tool relative to a fiducial. For example, a location of the treatment tool relative to a fiducial, as described in this disclosure, can be provided. The order of the operations, methods, mechanisms, etc. as described with respect to FIG. 18 is intended to be illustrative in nature, and not limited in scope.

In one or more various aspects, related systems include but are not limited to circuitry and/or programming for effecting the herein-referenced method aspects; the circuitry and/or programming can be virtually any combination of hardware, software, electromechanical system, and/or firmware configurable to effect the herein- referenced method aspects depending upon the design choices of the system designer.

4. Conclusion

This disclosure provides a number of embodiments of the treatment limiter mechanism. The embodiments of the treatment limiter mechanism as described with respect to this disclosure are intended to be illustrative in nature, and are not limiting its scope.

Those having skill in the art will recognize that the state of the art in computer, controller, communications, networking, and other similar technologies has progressed to the point where there is little distinction left between hardware, firmware, and/or software implementations of aspects of systems, such as may be utilized in the treatment limiter mechanism. The use of hardware, firmware, and/or software can therefore generally represent (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer and/or designer of the treatment limiter mechanism may opt for mainly a hardware and/or firmware vehicle. In alternate embodiments, if flexibility is paramount, the implementer and/or designer may opt for mainly a software implementation. In yet other embodiments, the implementer and/or designer may opt for some combination of hardware, software, and/or firmware. Hence, there are several possible techniques by which the processes and/or devices and/or other technologies described herein may be effected, none of which is inherently superior to the other in that any vehicle to be utilized is a choice dependent upon the context in which the vehicle can be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

It is to be understood by those skilled in the art that, in general, that the terms used in the disclosure, including the drawings and the appended claims (and especially as used in the bodies of the appended claims), are generally intended as "open" terms. For example, the term "including" should be interpreted as "including but not limited to"; the term "having" should be interpreted as "having at least"; and the term "includes" should be interpreted as "includes, but is not limited to"; etc. In this disclosure and the appended claims, the terms "a", "the", and "at least one" positioned prior to one or more goods, items, and/or services are intended to apply inclusively to either one or a plurality of those goods, items, and/or services.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that could have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that could have A alone, B alone, C alone, A and B together, A and C together, B and C together, and/or A, B, and C together, etc.).

Those skilled in the art will appreciate that the herein-described specific exemplary processes and/or devices and/or technologies are representative of more general processes and/or devices and/or technologies taught elsewhere herein, such as in the claims filed herewith and/or elsewhere in the present application.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A treatment limiter apparatus, comprising:
a dynamic barrier having magnetorheologic fluid, the magnetorheologic fluid actuatable to change rheological state by application of an electrical voltage; and
a controller operably coupled to the dynamic barrier and configured to determine status information based at least in part on location or position of a medical treatment tool and status information based on location or position of a patient treatment site;
the controller configured to actuate the application of the electrical voltage to change rheological state of the dynamic barrier based at least in part on the status information.

2. The treatment limiter apparatus of claim 1, wherein the controller is configured to actuate the application of the electrical voltage based on status information indicative that the medical treatment tool is located proximate a non-treatment region of a patient.

3. The treatment limiter apparatus of claim 1, wherein the controller is configured to actuate the application of the electrical voltage and to cause a hardening of a portion of the magnetorheologic fluid based on status information indicative that the medical treatment tool is located proximate a non-treatment region of a patient.

4. The treatment limiter apparatus of claim 1, wherein the controller is configured to actuate the application of the electrical voltage and to cause a softening of a portion of the magnetorheologic fluid based on status information indicative that the medical treatment tool is located proximate a treatment region of a patient.

5. A method, comprising:
comparing, via a microprocessor, status information based at least in part on location or position of a medical treatment tool and status information based on location or position of a patient treatment site; and
modulating a rheological property of a dynamic barrier by applying an electrical voltage to a region including magnetorheologic fluid based upon analyzing the status information.

6. The method of claim 5, wherein comparing, via a microprocessor, the status information based at least in part on location or position of the medical treatment tool and the status information based on location or position of the patient treatment site includes comparing medical treatment tool location or position information to fiducial position associator data indicative of a location of a patient.

7. The method of claim 5, wherein comparing, via a microprocessor, the status information based at least in part on location or position of the medical treatment tool and the status information based on location or position of the patient treatment site includes comparing a medical treatment tool location to a fiducial location.

8. The method of claim 5, wherein modulating the rheological property of the dynamic barrier includes causing a portion of the magnetorheologic fluid to harden when the comparing indicates that a medical treatment tool is located proximate a non-treatment region of the patient.

9. The method of claim 5, wherein modulating the rheological property of the dynamic barrier includes causing a portion of the magnetorheologic fluid to softened when the comparing indicates that a medical treatment tool is located proximate a non-treatment region of the patient.

10. The method of claim 5, further comprising:
deactivating the medical treatment tool when the comparing indicates that the medical treatment tool is located proximate a non-treatment region of the patient.

11. The method of claim 5, further comprising:
activating the medical treatment tool when the comparing indicates that the medical treatment tool is located proximate a treatment region of the patient.

12. A treatment limiter apparatus, comprising:
a dynamic magnetorheologic fluid barrier actuatable between a first rheological state and a second rheological state in the presence of an applied electrical voltage, wherein in the second rheological state the barrier blocks treatment access to a portion of a patient; and
a controller operably coupled to the dynamic magnetorheologic fluid barrier, the controller configured to
detect a location of a medical treatment tool relative to a treatment location on the patient and relative to one or more fiducial elements, and to
compare the medical treatment tool location to the medical treatment location information and to actuate the magnetorheologic fluid between a first rheological state and a second rheological state based on the comparison.

13. The treatment limiter apparatus of claim 12, wherein the controller is configured to actuate the magnetorheologic fluid between the first rheological state and the second rheological state by the application of an electrical voltage.

14. A method, comprising:
using a microprocessor to compare medical treatment tool location information to treatment location information of a patient; and
modulating a rheological property of a dynamic barrier by applying an electrical current to a region including magnetorheologic fluid when the comparing indicates that the medical treatment tool is located proximate a non-treatment region of the patient.

15. The method of claim 14, wherein modulating the rheological property of the dynamic barrier includes hardening a portion of the dynamic barrier element when the comparing indicates that a medical treatment tool is located proximate a non-treatment region of the patient.

16. The method of claim 14, wherein modulating the rheological property of the dynamic barrier includes applying an electrical voltage to the dynamic barrier when the comparing indicates that a medical treatment tool is located proximate a non-treatment region of the patient.

17. The method of claim 14, wherein modulating the rheological property of the dynamic barrier includes causing a change to a rheological property of the dynamic barrier in response to identifying at least one location of the medical treatment tool relative to a fiducial.

18. The method of claim 14, wherein modulating the rheological property of the dynamic barrier includes causing the dynamic barrier to harden when the medical treatment tool is located proximate the non-treatment region of the patient and causing the dynamic barrier to soften when the medical treatment tool is located proximate a treatment region of the patient.

19. The method of claim 14, further comprising:
modulating the rheological property of the dynamic barrier element based on a comparison indicative that the medical treatment tool is located proximate a treatment region of the patient.

20. A method, comprising:
comparing, via a microprocessor, medical treatment tool location information to treatment location information of a patient;

modulating a rheological property of a dynamic barrier when the comparing indicates that the medical treatment tool is located proximate a non-treatment region of the patient; and deactivating the medical treatment tool when the comparing indicates that the medical treatment tool is located proximate the non-treatment region of the patient.

21. The method of claim 20, wherein modulating the rheological property of a dynamic barrier includes causing the dynamic barrier to block treatment access to a portion of a patient.

22. The method of claim 20, wherein modulating the rheological property of a dynamic barrier includes causing the dynamic barrier to block treatment access to a portion of a patient by hardening.

* * * * *